(12) United States Patent
Zegarelli

(10) Patent No.: US 11,324,447 B2
(45) Date of Patent: May 10, 2022

(54) ORAL DATA COLLECTING DEVICE FOR DIAGNOSIS OR PROGNOSIS

(71) Applicant: Peter John Zegarelli, Sleepy Hollow, NY (US)

(72) Inventor: Peter John Zegarelli, Sleepy Hollow, NY (US)

(73) Assignee: Emanate Biomedical, Inc., New York, NY (US)

( * ) Notice: Subject to any disclaimer, the term of this patent is extended or adjusted under 35 U.S.C. 154(b) by 26 days.

(21) Appl. No.: 16/392,195

(22) Filed: Apr. 23, 2019

(65) Prior Publication Data

US 2019/0246980 A1 Aug. 15, 2019

Related U.S. Application Data

(62) Division of application No. 15/175,345, filed on Jun. 7, 2016, now Pat. No. 10,314,537.

(51) Int. Cl.
| | |
|---|---|
| *A61B 5/00* | (2006.01) |
| *A61B 5/01* | (2006.01) |
| *A61B 5/03* | (2006.01) |
| *A61B 5/083* | (2006.01) |
| *A61B 5/145* | (2006.01) |
| *A61B 10/00* | (2006.01) |

(52) U.S. Cl.
CPC ............ *A61B 5/682* (2013.01); *A61B 5/0002* (2013.01); *A61B 5/01* (2013.01); *A61B 5/038* (2013.01); *A61B 5/0833* (2013.01); *A61B 5/0836* (2013.01); *A61B 5/14539* (2013.01); *A61B 5/4547* (2013.01); *A61B 5/4552* (2013.01); *A61B 10/0051* (2013.01); *A61B 2562/028* (2013.01)

(58) Field of Classification Search
None
See application file for complete search history.

(56) References Cited

U.S. PATENT DOCUMENTS

| 4,629,424 A | 12/1986 | Lauks et al. |
| 5,204,670 A | 4/1993 | Stinton |
| (Continued) | | |

FOREIGN PATENT DOCUMENTS

| WO | 2015049321 | 4/2015 |
| WO | 2017197262 A1 | 11/2017 |

OTHER PUBLICATIONS

International Search Report and Written Opinion of the International Searching Authority (ISA/US) dated Jul. 1, 2019 issued in Application No. PCT/US19/17223 filed on Feb. 8, 2019.

(Continued)

*Primary Examiner* — Brian T Gedeon
(74) *Attorney, Agent, or Firm* — Sorell, Lenna & Schmidt, LLP; William D. Schmidt, Esq.

(57) ABSTRACT

An apparatus that monitors information associated with an oral cavity is provided, the apparatus comprising: a three-dimensional oral appliance; a data collection device having at least one sensor and/or hydrogel like material configured to sense the information associated with the oral cavity; an interface device cooperatively coupled to the data collection device, the interface device configured to transfer the information from the sensor device to a receiving device external to the oral cavity or the entire device is analyzed.

6 Claims, 24 Drawing Sheets

(56) References Cited

U.S. PATENT DOCUMENTS

| | | |
|---|---|---|
| 5,245,592 A | 9/1993 | Kuemmel et al. |
| 5,626,537 A | 5/1997 | Danyo et al. |
| 6,607,387 B2 | 8/2003 | Mault |
| 7,708,557 B2 | 5/2010 | Rubbert |
| 8,104,324 B2 | 1/2012 | Hennig et al. |
| 8,113,837 B2 | 2/2012 | Zegarelli |
| 8,505,541 B2 | 8/2013 | Bardach et al. |
| 8,771,149 B2 | 7/2014 | Rahman et al. |
| 9,089,388 B2 | 7/2015 | Zegarelli |
| 2004/0110110 A1 | 6/2004 | Chishti et al. |
| 2006/0115790 A1 | 6/2006 | Alon et al. |
| 2006/0199141 A1 | 9/2006 | Wen |
| 2007/0106138 A1 | 5/2007 | Beiski et al. |
| 2007/0207434 A1 | 9/2007 | Kuo et al. |
| 2008/0044797 A1 | 2/2008 | Bardach et al. |
| 2009/0136893 A1 | 5/2009 | Zegarelli |
| 2009/0146344 A1 | 6/2009 | El-Siblani |
| 2011/0136077 A1 | 6/2011 | De Moyer |
| 2013/0052613 A1 | 2/2013 | Chetiar et al. |
| 2013/0253286 A1 | 9/2013 | Fridman |
| 2014/0011162 A1* | 1/2014 | Zegarelli .................. A61B 1/24 433/215 |
| 2014/0177880 A1* | 6/2014 | Kassayan ............ G10L 21/0216 381/151 |
| 2015/0112697 A1 | 4/2015 | Bradley |
| 2015/0282913 A1 | 10/2015 | Zegarelli |
| 2016/0242692 A1* | 8/2016 | McAuliffe .............. G06F 30/00 |
| 2016/0278902 A1 | 9/2016 | Zegarelli |
| 2017/0007386 A1 | 1/2017 | Mason et al. |
| 2017/0028178 A1 | 2/2017 | Skoda |
| 2017/0132393 A1 | 5/2017 | Natarajan et al. |
| 2017/0232300 A1 | 8/2017 | Tran et al. |

OTHER PUBLICATIONS

International Search Report and Written Opinion of the International Searching Authority (ISA/US) dated Jun. 21, 2019 issued in Application No. PCT/US19/17225 filed on Feb. 8, 2019.

* cited by examiner

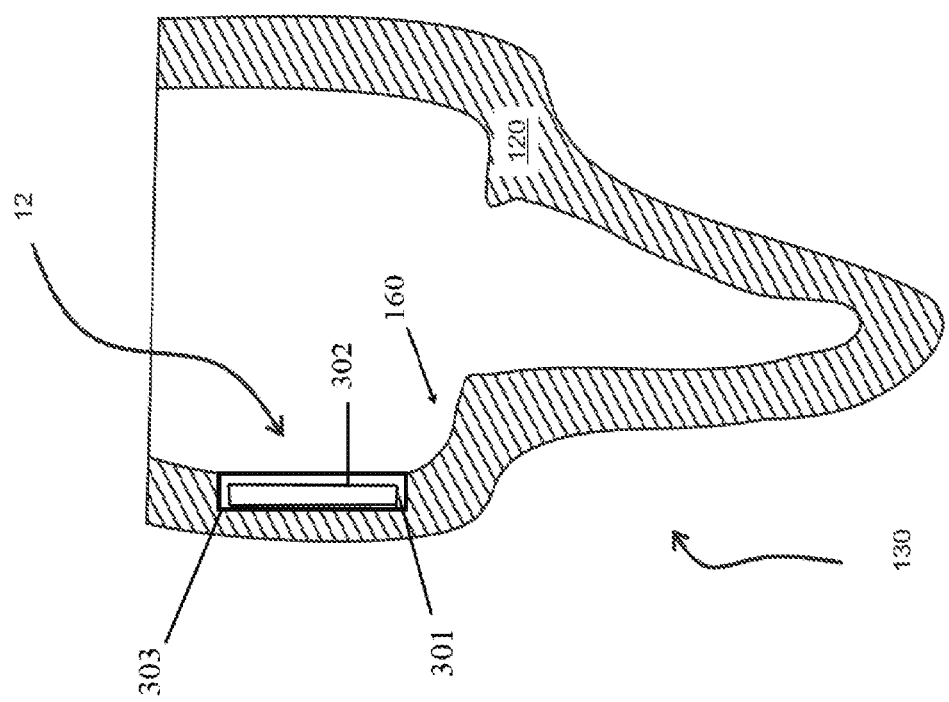

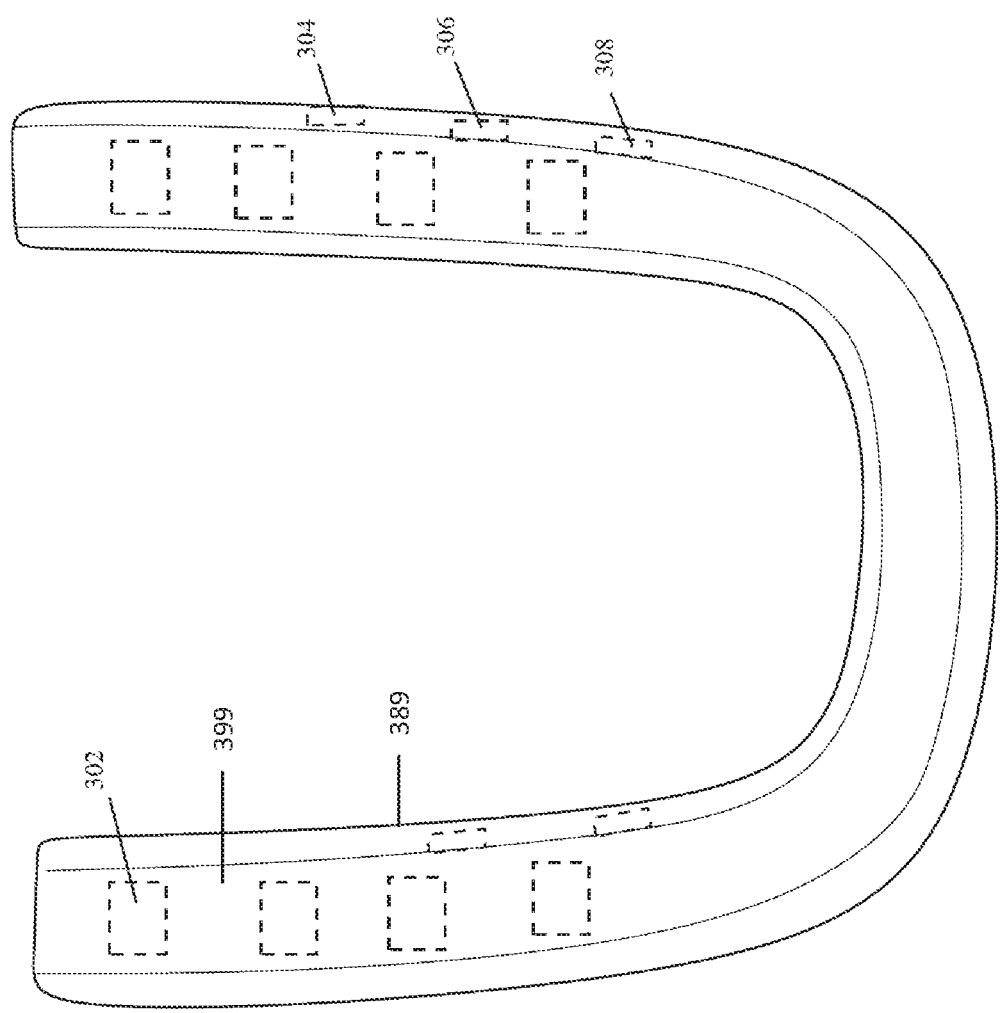

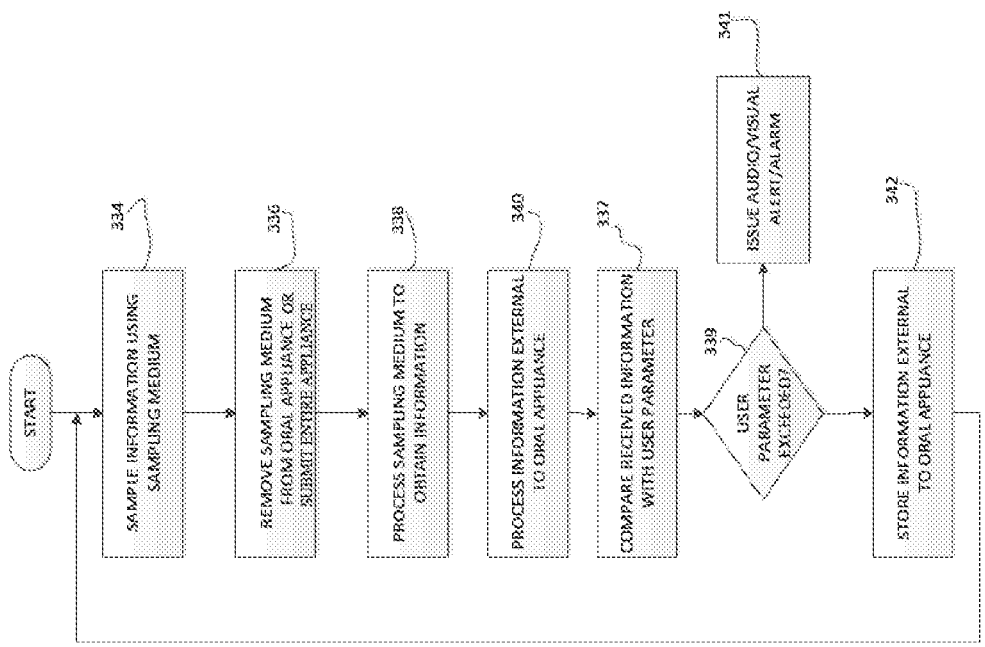

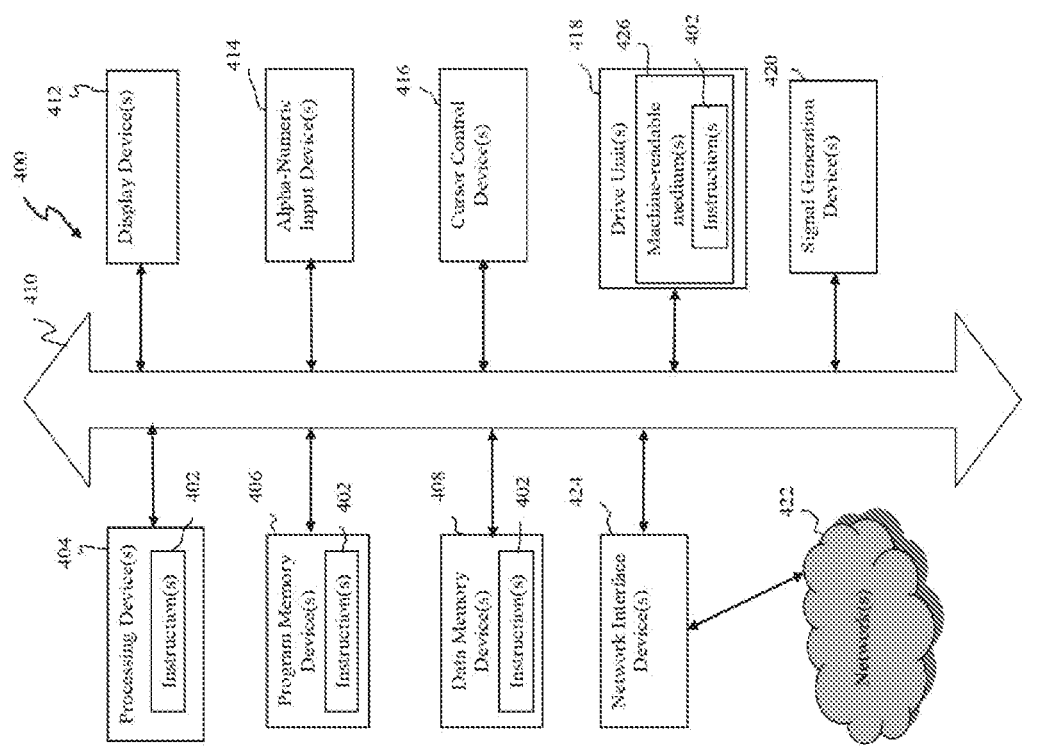

ORAL DATA COLLECTING DEVICE FOR DIAGNOSIS OR PROGNOSIS

BACKGROUND

Oral appliances that allow drug delivery to the oral cavity have been developed that have a reservoir to hold liquid medicaments or a cargo area that have a foam disposed in the cargo area for delivery of the drug to the oral cavity. These oral appliances are available in universal sizes to generically fit adults or are custom made for a precise fit to the teeth and gums of the individual patient.

Oral appliances that are provided in universal sizes often do not adequately match the patient's actual oral cavity characteristics. This can lead to poor contact in areas where such oral appliances are adapted to deliver the drug. Custom made oral appliances present a better fit to the patient's oral cavity since they are fabricated to match the actual oral cavity in which they are employed.

Based on the above, new oral appliances are needed that improve measurement of the biological activity occurring in the oral cavity, for example, saliva activity, pressure, oxygen content, temperature, pH, bacteriologic/viral/cellular assays, gingival/periodontal fluids and exudates or other bodily fluids or exudates such as phlegm or sputum or other parameters in order to more accurately treat diseases on an individual basis. Such oral appliances may be easily manufactured and, in some embodiments, based on the patient's actual oral cavity architecture so that they are easy and comfortable for the patient to wear, or the oral appliance can be a universal fit appliance for the person to wear.

SUMMARY

New oral appliances are provided that apply sensors to an oral cavity in a three dimensional manner. In various embodiments an oral appliance is provided for sensing various biological characteristics including temperature, pH, $O_2$, and $CO_2$, content in saliva or sulcular assays or other conditions in the mouth.

The oral appliance contains an interior surface having a sensor array disposed in or on at least a portion of and/or the entire interior surface of the oral appliance. In some embodiments, the oral appliance can be a universal oral appliance to fit most users. In some embodiments, the oral appliance is a custom fit oral appliance where the interior surface of the oral cavity is formed to fit contours of at least the portion of the teeth and/or soft tissue areas inside the oral cavity and is configured for supporting and holding the sensor array in contact with at least the portion of the teeth and/or soft tissue areas inside the oral cavity to assay the environment. In various embodiments, the oral appliance is monolithic or a single piece and the interior surface is individually custom fit and formed to fit contours of the teeth and/or soft tissue areas inside the oral cavity of a specific person and no other. Unlike prior art oral appliances, an embodiment of the oral appliance of the present application has differing types of sensor arrays as part of the appliance. In certain embodiments, the oral appliance comprises several variations configured to assay various substances.

In some embodiments, the sensors can be at discrete positions on the exterior surface of the oral appliance, and/or on the interior surface of the oral appliance to sense the biological environment within the oral cavity and transmit the data to a remote computer of the user, and/or health care provider to monitor, diagnose or prognose the condition of the wearer's oral cavity over a continuous period of time (e.g., minutes, hours, 24 hours, 48 hours, 1 week).

In certain embodiments, the material of the oral appliance is a polymer gel, a hydrogel, a brush polymer or a combination thereof, or of some sponge like character or tampon material. In some embodiments, the hydrogel comprises, consists essentially of or consists of an amount from about 10% to about 90% by weight, from about 20% to about 80% by weight, from about 30% to about 70% by weight, from about 40% to about 60% by weight of the oral appliance. The material employed serves to absorb cells, chemical secretions, and other biomaterials. Once the oral appliance has been used for a period of time to allow sampling of cells, chemical secretions, and other biomaterials, the user removes the appliance and it is then analyzed.

In some embodiments, the oral appliance is optionally constructed from a digital data set representing at least a portion of or all of the teeth and/or soft tissue areas inside the oral cavity. This permits precise placement of sensors at positions of interest.

In some embodiments, there is an oral appliance for assaying chemical properties or environmental conditions at a portion of teeth and/or soft tissue areas inside an oral cavity, the oral appliance comprising an interior surface having a sensor array disposed in or on at least a portion of and/or all of the interior surface of the oral appliance, the interior surface being formed to fit contours of at least the portion of the teeth and/or soft tissue areas inside the oral cavity and being configured for holding the sensor array in contact with at least the portion of the teeth and/or soft tissue areas inside the oral cavity to permit measurement of the aforesaid chemical and/or environmental properties within the oral cavity.

In some embodiments, there is an oral appliance for improving assays of saliva collection. Presently, assays of saliva utilize a single "spit in time" which is limited in quality and quantity since the assays only measure a moment. A person can be dehydrated, have just eaten or is on medications which dry the mouth, all of which affect the quality and quantity of the saliva. Sputum and phlegm tests which measure infections in the breathing passages including the sinuses can be assayed with this oral appliance embodiment.

In some embodiments, there is a computer implemented method of making an oral appliance, the method comprising: creating a digital record of a patient's oral cavity which is called the Base Image (BI). The BI can be obtained by the conventional analog method of taking an impression of the patient's mouth with common impression materials such as alginate, polyvinyls, silicones or other such materials or may be taken with various scanning devices for a more direct digital record of the topography of the patient's mouth. With the analog method, either the impression would be poured with dental stone and the positive model would be scanned or the impression itself, the negative, would be scanned yielding a digital record of the BI.

The BI is a permanent record of the topography of the patient's mouth and is digitally stored to provide a base record and also for future digital manipulations to form oral appliances. Computerized program manipulations are made to create the first digital image (Dig1) of at least a portion of the teeth, and/or soft tissue of the oral cavity. Dig1 is an additive process in which programmatically a platform appliance image is digitally layered over the BI. Dig1 is the platform carrier for placing sensors at discrete positions in the mouth or a sensor web in the mouth. A second subtractive process of the BI is programmatically made and this image is stored as the second digital image (Dig2). Dig2 is a three dimensional representation of the geographic area to have the sensors disposed in the oral appliance. The second digital image (Dig2) is a subtractive process made through program manipulations where spaces in the oral appliance are generated to dispose the sensors against at least a portion of the teeth and/or soft tissue of the oral cavity; the second digital image is subtracted from the corresponding area of the first digital image (Dig1) which forms a final third digital image (Dig3) of the oral appliance with indentations formed by the second digital image Dig2 and into which sensors are disposed at an area of interest. It is from this third digital image that the appliance is manufactured and made virtually through the computer.

In some embodiments, the BI is a permanent record of the topography of the patient's mouth and is digitally stored to provide a base record and also for future digital manipulations to form oral appliances. Computerized program manipulations are made to create the first digital image (Dig1) of at least a portion of the teeth, and/or soft tissue of the oral cavity. Dig1 is an additive process in which programmatically a platform appliance image is digitally layered over the BI. Dig1 is the platform carrier for placing sensors at discrete positions in the mouth or a sensor web in the mouth. A second additive process of the BI is programmatically made and this image is stored as the second digital image (Dig2). Dig2 is a three dimensional representation of the geographic area to have the sensors disposed in the oral appliance. The second digital image (Dig2) is an additive process made through program manipulations where spaces in the oral appliance are generated to dispose the sensors against at least a portion of the teeth and/or soft tissue of the oral cavity; the second digital image is added to the corresponding area of the first digital image (Dig1) which forms a final third digital image (Dig3) of the oral appliance with indentations formed by the second digital image Dig.2 and into which sensors are disposed at an area of interest. It is from this third digital image that the appliance is manufactured and made virtually through the computer.

In some embodiments, there is a network based computer system for making an oral appliance pre-loaded with at least one sensor in at least one location. The network based computer system includes programming (either in the form of software, firmware, or hardware) for generating Dig1 data representing an additive overlay of at least a portion of the teeth and/or soft tissue areas of the oral cavity of a patient built upon the BI. The BI data then has one or more surface areas identified by a technician or doctor using the computer system to perform digital segmentation of at least a portion of the teeth and/or soft tissue areas of the oral cavity to identify areas of interest for sampling by sensors. Essentially, the original image of the mouth (BI) provides the template for creating the additive first digital image (Dig1) and the segmented second digital image (Dig2) through various program manipulations of the base image of the mouth (BI) to form a final showing the positions of the sensors in the third digital image of the mouth (Dig3) from which image the appliance will be fabricated.

In some embodiments, there is a computer readable storage medium storing instructions that, when executed by a computer, cause the computer to: receive BI data from an imaging device, from which image an additive manipulation is performed yielding the Dig1 data representing the platform carrier over at least a portion of the teeth and/or soft tissues areas of the oral cavity of a patient. The BI is then again manipulated by identifying at least one surface area thereof to generate a Dig2 data which represents indentations to be made in the interior surface of the Dig1 layered structure for acceptance of a sensor or multiple sensors at areas of interest. A merging of the Dig1 data with the additive or subtractive Dig2 manipulation forms the Dig3 data from which the oral appliance can be produced, wherein the Dig3 data comprises positions for at least one sensor to be placed in the oral cavity areas of interest.

In some embodiments, there is an oral appliance for collecting a sample from at least a portion of teeth and/or soft tissue areas inside an oral cavity, the oral appliance comprising an interior surface having an absorptive material disposed in or on at least a portion of and/or all of the interior surface of the oral appliance, the interior surface being formed to fit contours of at least the portion of the teeth and/or soft tissue areas inside the oral cavity and being configured for holding the absorptive material in contact with at least the portion of the teeth and/or soft tissue areas inside the oral cavity to collect the sample therefrom. The absorptive material follows surface areas of the mouth to be tested and is disposed in layers defined by the Dig2 manipulation of the BI and added to the Dig1 layer structure.

Briefly stated, a further embodiment provides a computer implemented method and computer system for producing an oral appliance including scanning an oral cavity to produce a three dimensional digital representation of an oral topography followed by presenting a display of the scan. The system accepts input indicating areas of interest to be sampled by sensors. A first 3D digital representation of a platform carrier based on the scan is created. A user inputs a sensor type to be employed and the system calculates an indentation size (area and depth) based on the sensor type and generates a second 3D digital representation of the indentation. The second 3D digital representation is subtracted from the first 3D digital representation to a form a third 3D digital representation which is used to operate a 3D printer to produce the oral appliance with the indentations for sensors.

In another embodiment, there is an apparatus that monitors information associated with an oral cavity, the apparatus comprising: a three-dimensional oral appliance; a data collection device having at least one sensor configured to sense the information associated with the oral cavity; an interface device cooperatively coupled to the data collection device, the interface device configured to transfer the information from the sensor device to a receiving device external to the oral cavity. In some embodiments, the information associated with the oral cavity comprises at least one of pH, temperature, pressure, $O_2$ content, $CO_2$ content, bacterial content, or saliva quantity/quality or gingival/periodontal fluids and exudates or other bodily fluids or exudates such as phlegm or sputum.

In another embodiment, there is a computer-readable medium for making an oral appliance containing a discrete region for placing a sensor to collect biological information about a patient's oral cavity, the computer-readable medium comprising instructions that, when executed by a processing device, cause the computer to: generate first digital data representing at least a portion of teeth and/or soft tissue areas of the oral cavity of the patient, the first digital data generated from an imaging device having a base image of the oral cavity; generate a second digital data from the base image by performing a digital segmentation of at least a portion of the teeth and/or soft tissue areas of the oral cavity to determine the discrete region of the oral cavity to place the sensor; and combine the first digital data (Dig1) and the second digital data (Dig2) to form a third digital data (Dig3) from which an oral appliance can be produced into 3D printing data, wherein the third digital data comprises the discrete region for placing the sensor to collect the biological information of the patient's oral cavity In another embodiment, there is a computer-readable medium comprising instructions that, when executed by a processing device, perform operations comprising: monitoring information associated with an oral cavity from a data collection device of a three-dimensional oral appliance; the data collection device having at least one sensor configured to sense the information associated with the oral cavity; and an interface device cooperatively coupled to the data collection device, the interface device configured to transfer the information from the sensor device to a receiving device external to the oral cavity.

In another embodiment, there is an oral appliance for collecting biological information about at least a portion of teeth and/or soft tissue areas inside an oral cavity, the oral appliance comprising an interior surface having a sampling medium disposed in or on at least a portion of and/or all of the interior surface of the oral appliance, the interior surface being formed to fit contours of at least the portion of the teeth and/or soft tissue areas inside the oral cavity and being configured for holding the sampling medium in contact with at least the portion of the teeth and/or soft tissue areas inside the oral cavity, the sampling medium configured to collect biological tissue from the oral cavity and be removed from the interior surface of the oral appliance. In some embodiments, the sampling medium is also configured to collect biological fluids, exudates or cells.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

The above, and other objects, features and advantages of the present disclosure will become apparent from the following description read in conjunction with the accompanying drawings, in which like reference numerals designate the same elements.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present disclosure, as defined solely by the claims, will become apparent in the non-limiting detailed description set forth below.

Furthermore, while various features and objects are presented in the above summary, said summary is not intended to limit the appended claims to coverage of embodiments which address any one, any combination, or all of the above noted features and objects.

BRIEF DESCRIPTION OF THE DRAWINGS

In part, other aspects, features, benefits and advantages of the embodiments will be apparent with regard to the following description, appended claims and accompanying drawings wherein:

FIG. 10B is the cross-sectional view of an area of the carrier shell of FIG. 1 taken along line IXb-IXb wherein a carrier shell and an area of interest housing the apparatus that monitors physical, chemical, biological, and/or environmental information associated with the oral cavity at a portion of the carrier shell adjacent a bottom portion of an upper molar area are depicted.

FIG. 10D is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity. In this view, a plurality of data collection devices are disposed in the interior surface and exterior surface of the oral appliance.

FIG. 14 is a flowchart of another embodiment of the oral appliance. Information is sampled using a sampling medium. The sampling medium is then removed from the oral appliance. The sampling medium is processed to obtain certain information. The information is processed external to the oral appliance. The received information is then compared to the user parameters of FIG. 13. If the user parameters have been exceeded (e.g., decrease in pH or oxygen content, decrease in electroconductivity, etc.), then an audio/visual alert or alarm is issued. The information is then stored external to the oral appliance.

FIG. 15 is a block diagram showing at least a portion of an exemplary machine in the form of a computing system that performs methods according to one or more embodiments disclosed herein.

Figure 1:
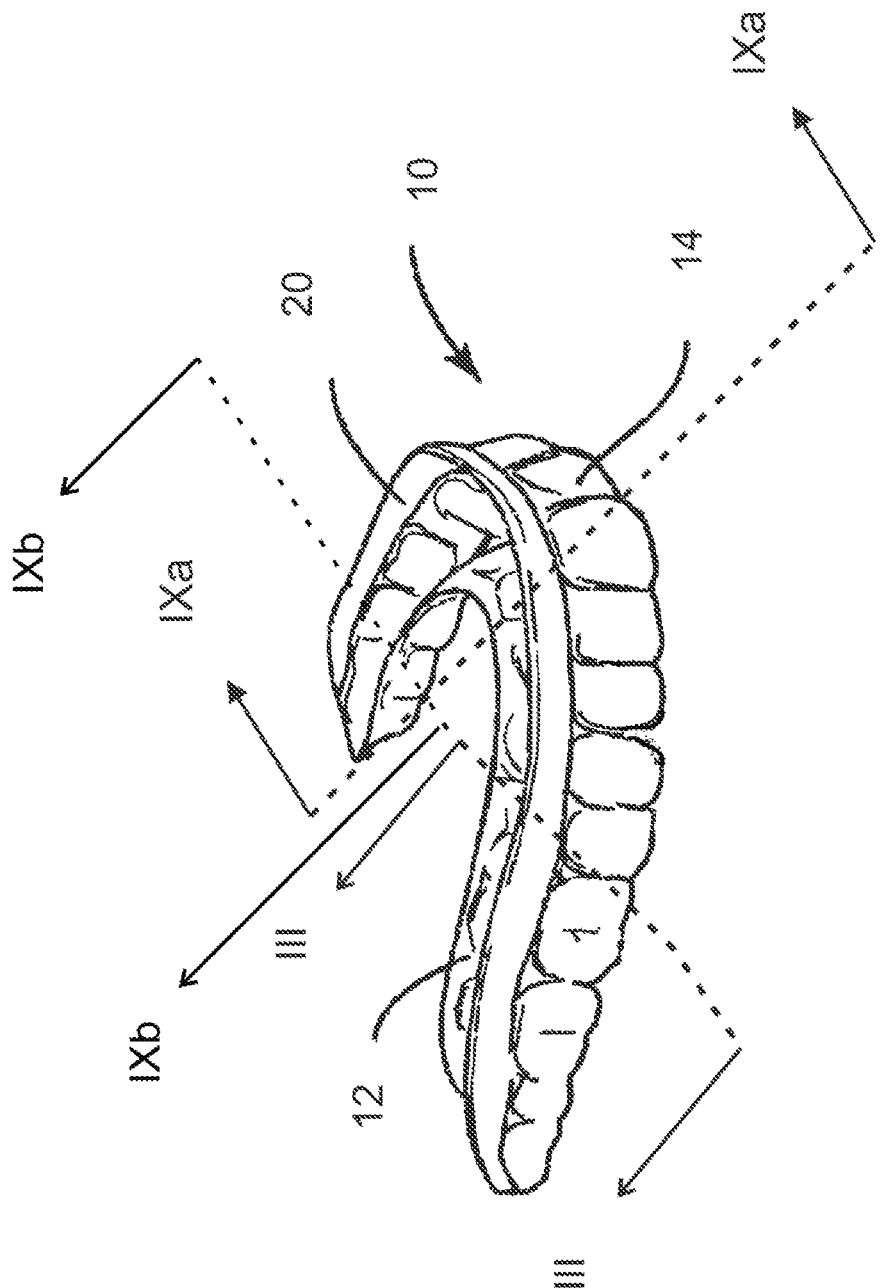
FIG. 1 is a perspective view of an embodiment of an oral appliance for covering upper teeth and/or soft tissues of a patient, the oral appliance being shown without teeth and/or soft tissues inserted in the oral appliance.

It is to be understood that the figures are not drawn to scale unless so indicated. Further, the relationship between objects in a figure may not be to scale, and may in fact have a reverse relationship as to size unless so indicated. The figures are intended to bring understanding and clarity to the structure of each object shown, and thus, some features may be exaggerated in order to illustrate a specific feature of a structure. Accordingly, the figures are not intended to limit the scope and breadth of the appended claims.

DETAILED DESCRIPTION

With regard to the following description, it is to be understood by those skilled in the art that unless a specific number of an introduced claim element is recited in the claim, such claim element is not limited to a certain number. For example, introduction of a claim element using the indefinite article "a" or "an" does not limit the claim to "one" of the element. Still further, the following appended claims can contain usage of the introductory phrases "at least one" and "one or more" to introduce claim elements. Such phrases are not considered to imply that the introduction of a claim element by the indefinite articles "a" or "an" limits any particular claim containing such introduced claim element to coverage of devices or processes containing only one such element or containing more than one such element, even when the same claim includes the introductory phrases "one or more" or "at least one."

It is to be further understood that claim terminology relating to elements A, B, and C recited as "one of A, B, and C" is intended to cover devices or processes having one or more of element A, or one or more of element B, or one or more of element C, and does not require the presence of three of such elements A, B, and C, nor exclude coverage of devices or processes including the presence of three of such elements A, B, and C. Likewise, recitation of "at least one of A, B, and C" is to be given the same interpretation. On the other hand, if it is intended to limit coverage of a claim to devices or processes including one of each of a set of elements, the phraseology "one of each of A, B, and C" or "at least one of each of A, B, and C" is used.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is also to be further understood that the doctrine of claim differentiation is to be applied across an independent claim and its dependents and is not intended to be applied across a plurality of independent claims. For example, term A in a first independent claim may be interpreted to have the same scope as term B in second independent claim, while if term A is in a first independent claim and term B further defines term A in claim dependent from the first independent claim, then term A must have a broader scope than term B. In other words, phrases that differ from one independent claim to another independent claim, may be interpreted to have equal scope and read on common structure yet present the structure using different terminology in order account for differing interpretation of phrase language.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

Headings where presented below are not meant to limit the disclosure in any way; embodiments under any one heading may be used in conjunction with embodiments under any other heading.

Oral Appliance

New oral appliances are provided that can provide diagnostic information derived from at least a portion of the teeth and/or soft tissues inside the oral cavity in a three-dimensional way. One advantage of the oral appliance, in some embodiments, is that it may be custom made to fit a specific patient. As used herein a "custom fit" oral appliance refers to an oral appliance prepared to correspond to at least a portion of the teeth or all of the teeth and soft oral tissues of a specific patient. Typically, the custom fit appliance is prepared by a dental care professional (e.g., dentist, oral surgeon, medical doctor, other health care professional, manufacturer, etc.). The custom fit oral appliance can be made from an impression mold, or using an analog or digital image capturing device. In some embodiments, the oral appliance provided by this disclosure can be a boil-and-bite prefabricated device or a stock oral appliance, which can be manipulated by the patient's fingers to shape it against the teeth and gums. This is not a custom oral appliance but can be manipulated by the patient to fit their mouth. As opposed to conventional oral appliances, the appliances provided herein can contain a sensor in a cargo area of the oral appliance that can be generated by 3D printing.

In some embodiments, the oral appliances disclosed herein can be universal, disposable, monolithic devices, manufactured in one continuous step(s), pre-loaded with one or more data collection devices (e.g., sensors or hydrogels) in or on at least a portion of the interior and/or exterior surfaces of the appliance, and can sense chemical, physical, and/or environmental parameters and/or collect biological material three dimensionally. In some embodiments, the oral appliance can be transparent. Still another advantage of the oral appliance is that, in various embodiments, it can be easily manufactured and is comfortable for the patient to use. Other advantages of the oral appliances include greater efficacy over conventional oral data collection techniques based on two-dimensional systems, user convenience, enhanced patient compliance, reduced temporal requirements to detect conditions, ease of use, and enhanced pressure applied to the gums.

In one embodiment, there is an oral appliance for monitoring at least a portion of teeth and/or soft tissue areas inside an oral cavity, the oral appliance comprising an interior surface having an apparatus disposed in or on at least a portion of and/or all of the interior surface of the oral appliance, the interior surface being formed to fit contours of at least the portion of the teeth and/or soft tissue areas inside the oral cavity and being configured to hold a data collection device associated with the apparatus in contact with at least the portion of the teeth and/or soft tissue areas inside the oral cavity to monitor a diagnostic area therein.

The soft tissue of the inside of the mouth, includes but is not limited to any soft tissue adjacent or between the teeth, including but not limited to the papilla, tissue of the upper and lower dental arches, marginal gingiva, gingival sulcus, inter-dental gingiva, gingival gum structure on lingual and buccal surfaces up to and including the muco-gingival junction and/or the palate and/or the floor of the mouth. In various embodiments, the soft tissue area includes the muco-buccal folds, hard and soft palates, lining mucosa, the tongue and/or attached gingival tissue. In various embodiments, the oral appliance receives one or more teeth including one or more molars, premolars, incisors, cuspids, tooth implant, or combination or portions thereof. In other embodiments, the one or more sensors and/or hydrogel contained in the oral appliance can be disposed anywhere in or on the interior or exterior surface of the oral appliance adjacent to the gum and/or other soft tissue areas of the oral cavity including the front, back, and occlusal surfaces of one or more teeth.

Referring to FIG. 1, an enlarged side view of an embodiment of the oral appliance 10 is illustrated, which has an interior surface 12 and an exterior surface 14, both comprising a polymer that can, in some embodiments, be in gel or hydrogel form.

The interior surface 12 contacts one or more teeth and/or soft tissue areas of a patient. The interior surface 12 is custom fit to the individual patient's mouth and configured to receive all or a portion of the teeth and/or soft tissue areas inside the mouth. In this view, the interior surface contacts the teeth and soft tissue. Oral appliances include, but are not limited to, oral trays, oral holders, oral covers, or the like that are designed to be placed within the oral cavity. The interior surface 12 and/or exterior surface 14 of the oral appliance contain one or more sensors and/or hydrogel disposed in or on the polymer and the one or more sensors and/or hydrogel can be disposed anywhere within or on the monolithic oral appliance. For example, the one or more sensors and/or hydrogel can be disposed at discrete positions adjacent to the diagnostic or prognostic areas or uniformly disposed throughout the device. As the interior and/or exterior surface of the oral appliance contacts the oral cavity, the one or more sensors and/or hydrogel come into contact with the desired detection site or pressure from the device contacting tissue or fluid at the detection site (e.g., gums, tissue, teeth, etc.).

In some embodiments, unlike orthodontic appliances, the one or more embodiments of the oral appliance are not designed to move teeth. Therefore, a plurality of oral appliances will be configured to hold the teeth in the same position within the appliance. The teeth position will not change. However, the one or more sensors and/or hydrogel disposed in or on the oral appliance will be in the same or different areas at different stages of the detection regimen with a variety of oral appliances. Thus, kits containing a plurality of devices can be provided with different detection stages from the data collection device (e.g., sensor, sensors, sensor array, and/or sensor web). Suitable sensors include, but are not limited to temperature sensors, pressure sensors, moisture sensors, light sensors, pH sensors, acceleration sensors, or like. These sensors in some embodiments, collect measurements from the patient's gums, teeth, saliva, and tongue, such as vital signs, respiratory measures, blood oxygen level, carbon dioxide levels, head motion, saliva chemistry, gingival chemistry, for example.

Figure 2:
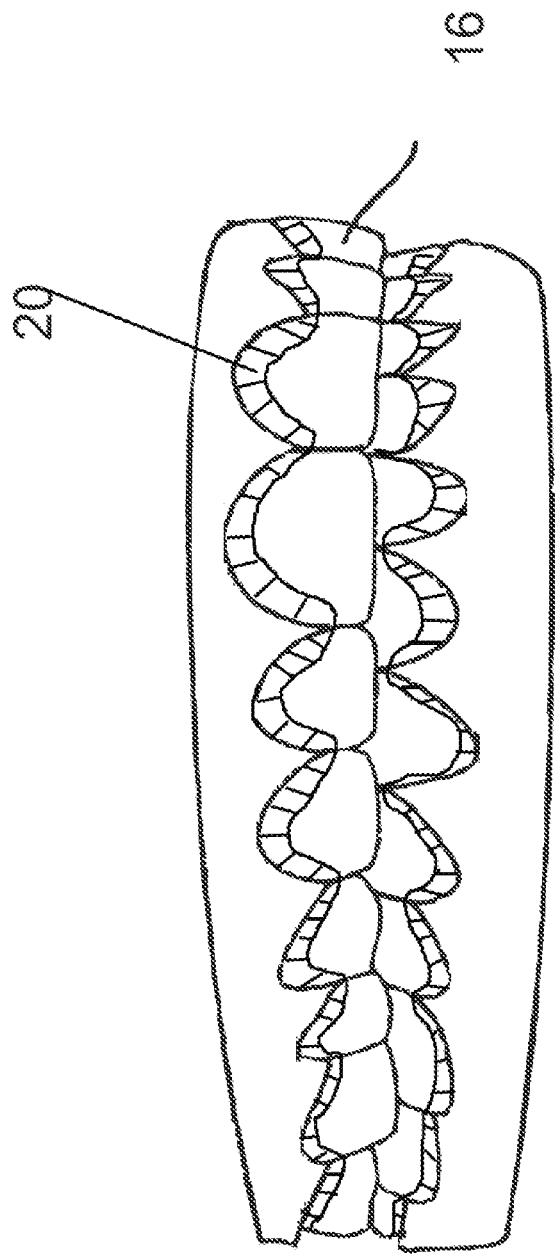
FIG. 2 is a front and right side elevation view of an embodiment of the oral appliance of FIG. 1 and a second oral appliance for covering lower teeth and/or soft tissues, wherein locations of sensors (small rectangles) are shown. In one embodiment, the sensors are situated adjacent to a gingival sulcus region.

FIG. 2 is an enlarged side view of an embodiment of an oral appliance. In this embodiment, the oral appliance is transparent and holds teeth 16 and or gums, which are covered by the oral appliance. The oral appliance includes a surface that contains one or more sensors and/or hydrogel as part of the polymer that, in use, monitors physical, chemical, biological, and/or environmental information, and/or collects biological material at or near the gingival sulcus 20.

Figure 3:
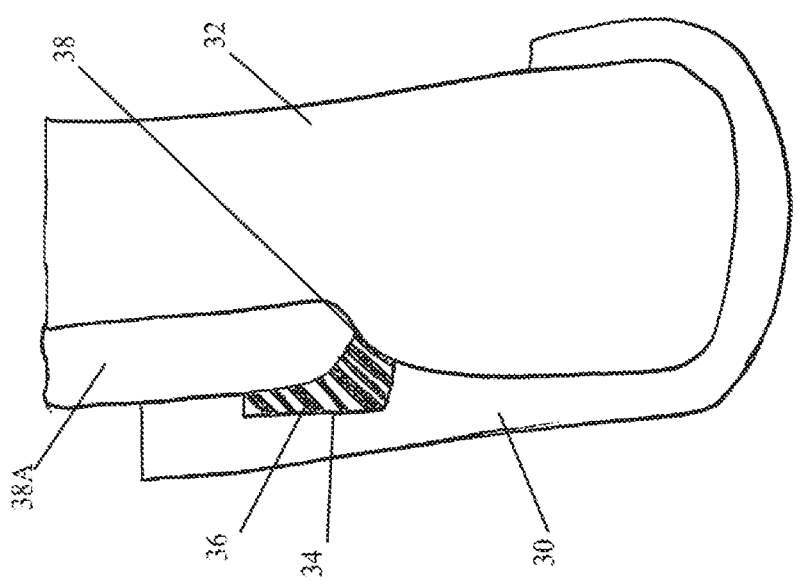
FIG. 3 illustrates a cross section of an embodiment of an oral appliance as a dental oral appliance having a sensor 36 disposed in an indentation defined by a Dig2 image.

FIG. 3 illustrates an enlarged cross-sectional view of the portion of the oral appliance 30 and its contact points surrounding a tooth 32 and an interior surface 34 having at least one or more sensors and/or hydrogel 36 which extends up and contacts the gingival sulcus region 38. It will be understood that the one or more sensors and/or hydrogel can be disposed throughout the interior and/or exterior of the device that contacts oral tissue. In the embodiment shown in FIG. 3, the interior of the device has one or more sensors and/or hydrogel disposed at discrete regions of the interior surface of the device adjacent to the areas to be detected (e.g., tooth and/or soft tissue areas).

Figure 4:
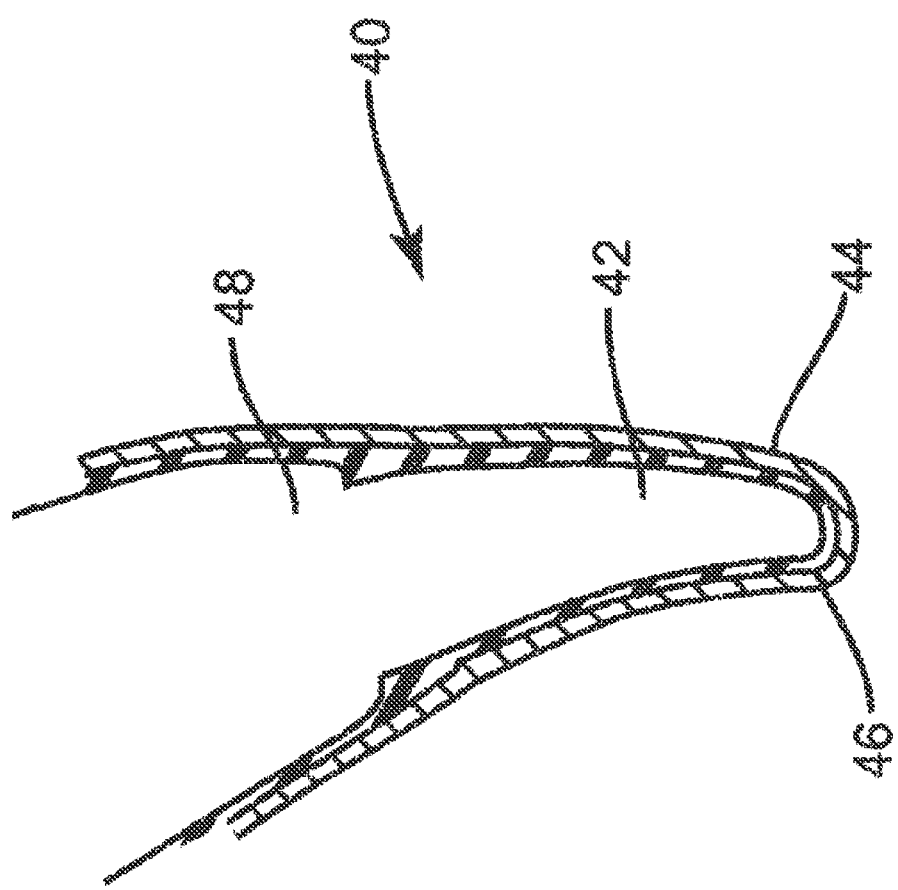
FIG. 4 illustrates an enlarged side cross sectional view of an embodiment of the oral appliance configured to correspond to and cover the tooth and soft tissue areas inside the oral cavity.

FIG. 4 illustrates an enlarged side cross-sectional view of an embodiment of the oral appliance 40 showing an outline of a tooth 42. The oral appliance 40 has an exterior surface 44 and interior surface 46. The interior surface of oral appliance 40 contains one or more sensors and/or hydrogel, which contacts tooth 42 up to gingival area 48. In the embodiment shown, the one or more sensors and/or hydrogel in the polymer layer extend and contact the buccal surfaces of the teeth and surrounding gingival tissue and over adjacent gingival tissue on a lingual side of the teeth. In some embodiments, the oral appliance extends over occlusal surfaces of the teeth and/or over lingual surfaces of the teeth in need of treatment.

In various embodiments, oral appliances disclosed herein can be manufactured to custom fit the patients' oral cavity as more particularly described below. Generally, a patient's mouth is first scanned utilizing a digital data acquisition tool. The data obtained in this manner can be used to form an initial digital record, the BI and that image is retained in a database. A dental professional can also obtain an initial record of the patient's oral cavity by taking an analog impression using alginate or other impression materials from which the analog model or impression will be scanned thus yielding the same BI. It is from this initial record of the patient's mouth, the BI that future oral appliances can be made. This image can be used as a permanent record of the patient's mouth, which can then be digitally manipulated yielding a three-dimensional representation of the tissues to be analyzed through the platform carrier, Dig1, and for various sensor and/or hydrogel locations, Dig2. The Dig2 can be the area that the sensors and/or hydrogel will be attached to the device and this can include cargo areas to hold the sensor. A virtual or real oral appliance, Dig3 is thereby formed by merging the additive digital image, Dig1, with the segmentally manipulated image, Dig2, to create the final detection image, Dig3. The Dig1 image merged with the Dig2 image creates the Dig3 image from which the oral appliance can be created. The BI provides an outline of at least a portion of and/or all the surfaces of the teeth, gingiva and/or other soft tissues, which a dental practitioner may wish to obtain information regarding. Other soft tissues of the oral cavity include without limitations, the palate, muco-buccal and muco-labial tissues, floor of the mouth, tongue, buccal and labial mucosae, and any other oral tissues. An authorized user can generate Dig1 by using software to create a layer over the teeth and gingiva that tightly approximate these tissues. The original image is then digitally enhanced to include a layer over the digital image. Digital image Dig1 resembles a virtual oral appliance, which can be used to create a real oral appliance. Dig1 is the platform carrier from which all future appliances will be based. With respect to Dig1, the BI of the patient's teeth and gums, has not been manipulated or modified by the computer at this point, but has had a digitally represented overlay of teeth and soft tissues. The additive process can be varied such that the oral appliance can be made thicker in some areas for stiffness and retention, such as over the teeth and thinner in other areas for flexibility and comfort, such as over the soft tissues. The platform carrier can also vary chemically in different regions such that it may have a chemically stiffer polymer in one region and a more flexible polymer in another region. Alternatively, the edge of the platform carrier can have a swellable hydrogel to press against the soft tissues and thereby lock in the oral appliance and lock out the saliva, thus preventing leakage out and leakage in. Other chemical or elastic formulations and permutations thereof can be mixed and matched to suit a desired result. The current analog model of manufacturing may not yield these variations.

In some embodiments, Dig1 comprises the virtual image of portions of the oral appliance. By using virtual three-dimensional (3D) imaging and 3D printing, one can utilize a gradient of physical and chemical characteristics to modify the oral appliance. The printer can make portions of the oral appliance thicker for stiffness or thinner for flexibility and comfort or include a cargo area for holding the sensor. These features may be programmable using a computer system. In some embodiments, the oral appliance can modulate materials in its composition to provide stiff or flexible variations while keeping the oral appliance at a uniform thickness.

The digital image is stored in a computer readable data storage medium of a computer. Computer readable media, for example, store data that is accessible by a computer, such as magnetic cassettes, flash memory cards, digital video disks, Bernoulli cartridges, random access memories (RAMs), read only memories (ROMs), and the like and may also be used in an exemplary operating environment. Computer readable media do not include signals.

Using computer software, an authorized user can generate a second digital image referred to as Dig2. The software generating Dig2 includes points or discrete regions on the teeth and/or gingiva or other soft tissues as boundaries corresponding to areas in the oral cavity that the dental practitioner may wish to diagnose. As used herein, the "gingival margin area" comprises an area within the oral cavity, which includes the gum line and the attached gingiva, including the sulcus of the gums. The gingival margin area includes about 2 to 3 mm of tooth above the gum line. In some embodiments, the points or the discrete regions may include buccal surfaces of the teeth, surrounding gingival tissue, occlusal surfaces of the teeth, lingual surfaces of the teeth, and/or adjacent gingival tissue on a lingual side of the teeth. Through software manipulation of the image of a patient's mouth, Dig2 can be added or subtracted according to point boundaries to a predetermined depth that corresponds to the desired thickness of the layer to be merged with Dig1. For example, in some embodiments, Dig2 can have a thickness layer of about 0.5 mm. This area is mapped out on the BI and an additive layer of 0.5 mm thickness is programmed onto the map. This is an additive or subtractive programming of three dimensional space which is then merged precisely onto Dig1 in the exact area from which it was virtually programmed. It is digital image Dig2, which contains the cargo area to hold the one or more sensors and/or hydrogel required to detect a selected pathology. Merging Dig1 with Dig2 creates the final appliance Dig3.

Figure 5:
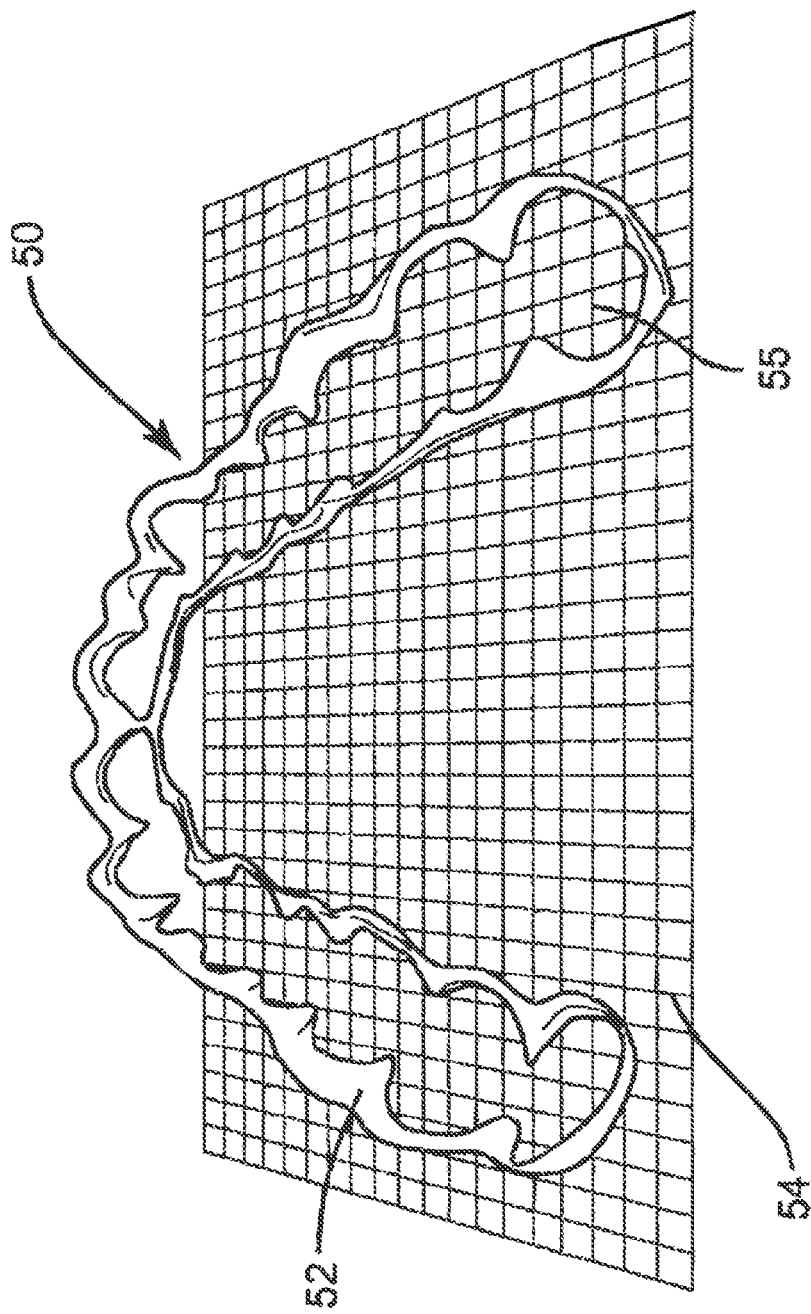
FIG. 5 illustrates an embodiment of a virtual image (Dig2) of the regions along the sulcus (gumline) where a sensor or a plurality of sensors are to be disposed at discrete or continuous regions corresponding to areas of interest.

FIG. 5 illustrates a virtual image of the polymer containing the one or more sensors and/or hydrogel for the oral appliance. This illustrates the additive or subtractive programming. In this case, the virtual 3D image 50 can be made by inputting data into the computer as to where the one or more sensors and/or hydrogel is to be disposed adjacent to the treatment areas of the oral appliance. The computer system can generate the interior surface 52 of the device where the one or more sensors and/or hydrogel will be disposed in the polymer and be adjacent to the diagnostic area. The 3D image can be generated by adding or subtracting space from the BI the soft and/or hard tissues to be monitored in a precise pattern, yielding an image of the targeted area, Dig2, to be merged with the original Dig1 platform device image. In some embodiments, the virtual 3D image 50 of the oral appliance will not have a floor to it as shown in the graph 55. This is because, in some embodiments, the 3D image generated will only have the discrete regions where the one or more sensors and/or hydrogel is to be disposed (Dig2). The remainder of the virtual image of the device can be constructed using a spatial geometric pattern 54 that can be used to add the virtual 3D image of the floor of the oral appliance and the exterior surface of the oral appliance. This includes height, width and depth to the virtual image. By utilizing the Dig2 software, a monitoring system can be created in which the one or more sensors and/or hydrogel can be applied to targeted teeth and/or tissues in a precise three dimensional manner. By adding the dimension of depth to the vertical and lateral dimension, an oral appliance modeled upon Dig2 can apply one or more sensors and/or hydrogel in a third dimension. The above Dig2 image is a precise addition or subtraction of the targeted tissue accomplished through computer programming, which is then saved to be used as further described below.

Once digital image Dig1 and digital image Dig2 have been generated, they can be merged via computer modeling to generate a third and final digital image, Dig3. In this manner, a virtual platform carrier oral appliance (Dig1) generated on the BI can be combined with a virtual digital image of the treatment area generated based on Dig2, such that the Dig2 image is precisely merged onto the Dig1 platform appliance on the inside of the Dig1 oral appliance to correspond to the exact area from which it was generated. As a result, Dig1 can be merged with an additive or subtractive process Dig2 to create a final computer enhanced image Dig3, which is a unique virtual three-dimensional image of the oral appliance including all or a portion of the oral appliance that contains one or more sensors and/or hydrogel in the areas adjacent to the diagnostic areas of the oral cavity that are unique to a given patient.

In some embodiments, it is contemplated that only the surfaces of the teeth will be detected and not the gums or only the gums will be detected.

Generating oral appliances that can provide three dimensional diagnostic assays can be used effectively for detecting and/or monitoring different conditions of the oral cavity. In other embodiments, a bulge can be placed on the exterior surface of the oral appliance that corresponds to the lower jaw and the lingual aspect, which faces the floor of the mouth and the lingual veins. In this process, Dig1 is obtained as before, however, Dig2 is created through the additive process of creating a bulge upon the exterior surface of Dig1. The bulge generated with Dig2 can hold the one or more sensors and/or hydrogel to be applied to the oral cavity. Oral appliances having an external surface having a bulge can be useful in detecting and/or monitoring many diseases and can assay saliva from all areas of the mouth as well as pre-cancerous, cancerous cells and/or other markers from the mouth, lungs, trachea, esophagus, stomach, sinuses of other areas of the body.

In another aspect, a virtual oral appliance Dig3 can be generated, which can be used by a dental professional to treat halitosis. The tongue has a rough surface due to the papillae on the tongue. This roughness creates millions of tiny spaces among the papillae that harbor microorganisms which frequently cause halitosis. In this aspect, the palate cover and the palatal aspects of the upper jaw form the external surface of the Dig1 virtual oral appliance. As a result, the Dig2 virtual oral appliance can be generated by adding a roughened surface that is Velcro-like in texture, which would include one or more sensors and/or hydrogel to detect volatile sulfur compounds produced by the microorganisms harbored among papillae and which cause halitosis and can detect neoplastic cells or other organisms, bacterial or fungal for example. A virtual Dig3 oral appliance generated based on the resulting merger of Dig1 and Dig2 can be used as a scouring pad to assay the tongue and then formulate the proper treatment regimen to resolve the halitosis. By closing the mouth and rubbing the tongue against the palate and the teeth, a patient could physically "Pap smear" the tongue in a scraping and/or rubbing motion. The rough, scouring pad surface of Dig3 covering the upper jaw and palate (roof of the mouth) can physically open and scrub the tiny spaces between papillae, thereby enabling increased sensitivity to detection of chemical, physical, and/or environmental parameters associated with halitosis. Simple scraping the tongue usually elicits a gag reflex. When one closes their mouth and rubs their tongue against the roof of their mouth, there is no gag reflex, thus when rubbing the tongue to the palate with the above described oral appliance, one will physically scrape the tongue and collect the material into the appliance which is then analyzed for proper treatment. FIG. 5A illustrates an enlarged view of a virtual image (Dig2) of the regions along the sulcus (gumline) 56 where the one or more sensors and/or hydrogel of the oral appliance will be loaded in a polymer gel material.

Figure 5B:
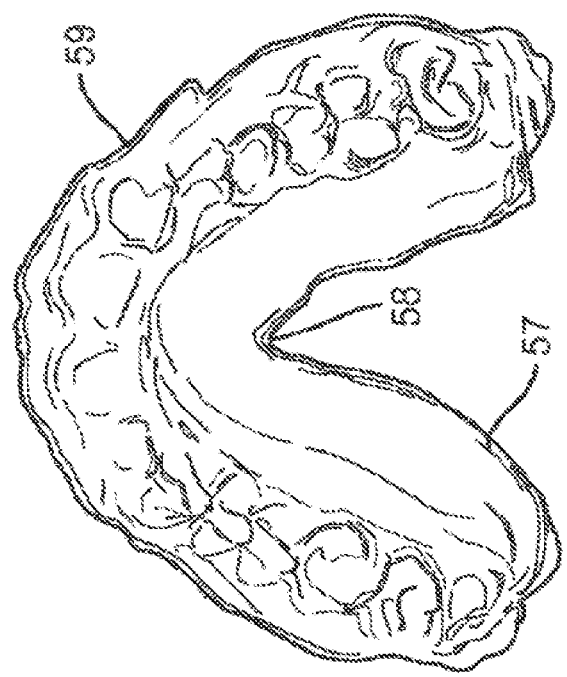
FIG. 5B illustrates an enlarged interior view of a virtual image (Dig1) of the oral appliance that is made by taking the BI of the oral cavity and creating a digital image that adds layers over the oral cavity including the teeth, gums, soft tissue areas and/or the palate, where Dig1 does not show locations corresponding to areas where the sensor is going to be disposed.
Figure 5A:
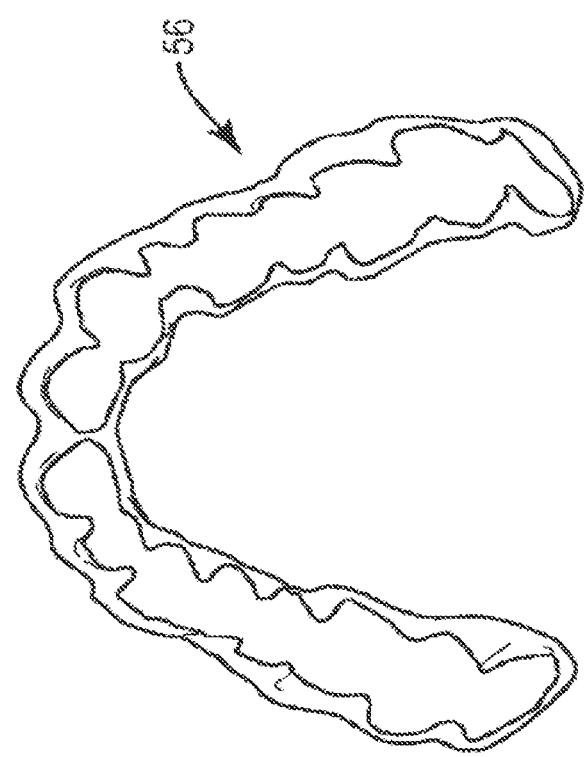
FIG. 5A illustrates an enlarged view of a virtual image (Dig2) of the regions along the sulcus (gumline) where sensors for taking measurement or hydrogel for sampling cells or other biological samples are disposed.

FIG. 5B illustrates an enlarged view of a virtual image (Dig1) of the oral appliance 59 that is made by taking a baseline digital image of the oral cavity and creating a digital image that corresponds to or layers over the oral cavity including the teeth, gums, soft tissue areas, and/or the palate. Dig1 does not have the virtual image of where the one or more sensors and/or hydrogel is to be disposed. The lower portion of the virtual oral appliance corresponds to and will contact portions of the tongue and hard palate 58 as well as the soft palate 57.

Figure 5C:
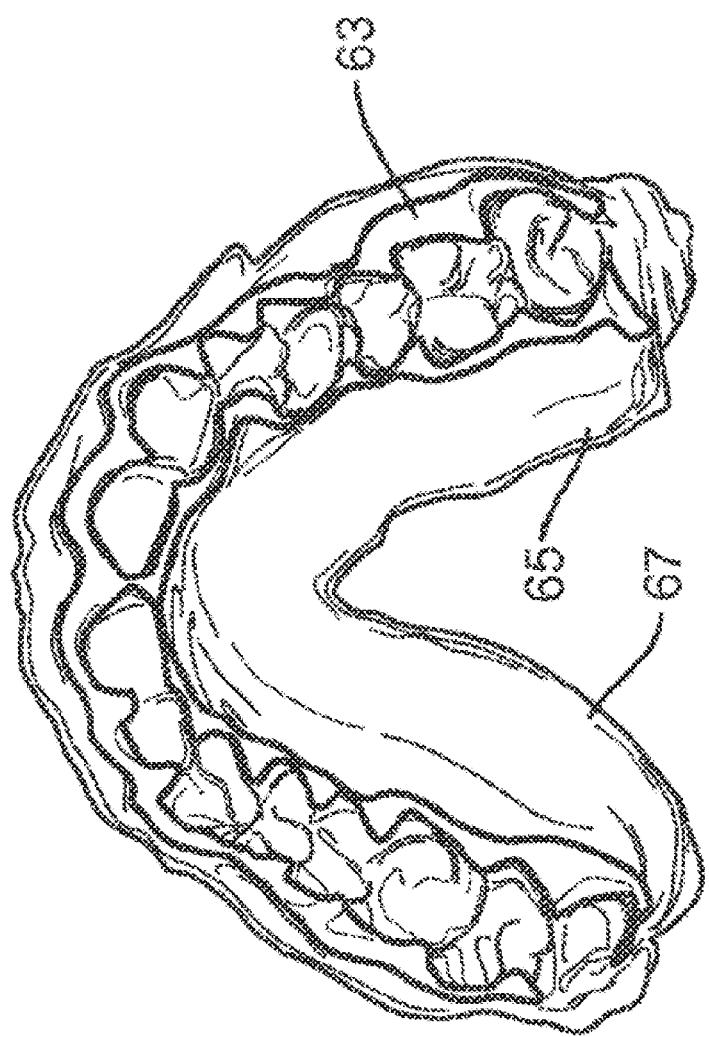
FIG. 5C illustrates an enlarged interior view of a virtual image (Dig3) of the oral appliance wherein the virtual image is a subtraction of the Dig2 digital data from the BI data, from which the oral appliance is produced that has regions along the sulcus (gumline) wherein a polymer gel material for sampling or a sensor, sensor web, sensors, or an array of sensors are disposed.

FIG. 5C illustrates an enlarged view of a virtual image (Dig3) of the oral appliance. The virtual image is the merging of the Dig1 data and the additive or subtractive data of Dig2, from which the oral appliance can be produced that has regions along the sulcus (gumline) 63 where the one or more sensors and/or hydrogel of the oral appliance will be loaded in a polymer gel material. The lower portion of the virtual oral appliance corresponds to and will contact portions of the tongue and hard palate as well as the soft palate 65 and textured, palatal scouring pad 67 along each side of the oral cavity. It is from Dig3 that the oral appliance can be manufactured.

By utilizing an oral appliance manufactured based on a virtual Dig3 oral appliance, the tongue of a patient can be assayed in part, for halitosis, fungal or other infections, through rubbing, while the remaining portion of the oral appliance, both interior and exterior aspects of which can be used to detect chemical, physical, neoplasms, and/or environmental parameters from virtually every surface of the oral cavity in a long and sustained manner. In this embodiment, Dig2 can additively or subtractively create a layer for the entire inside of the oral appliance and additively add a layer to the non-palatal portion of the upper oral appliance and the entire outer portion of the lower oral appliance. Both upper and lower oral appliances can apply one or more sensors and/or hydrogel to the entire mouth; inside and out. Held by the teeth and gum, the upper and lower oral appliances can apply one or more sensors and/or hydrogel through passive contact directly to the tissues. When one closes their mouth, there is no open space since the soft tissues collapse against each other and the hard tissues, such that the upper and lower appliances contact all the tissues in a sustained manner. As a result, a complete assay of the entire soft tissues of the mouth can be obtained to collect data of every hard and soft tissue.

In other aspects, tooth loss, gingival and bone grafting procedures, implants, and placement of regenerative tooth processes can also be monitored by the methods described in this disclosure. In various other aspects, the three dimensional methods described in this disclosure can be useful to monitor other diseases or surgical procedures of the body as a whole.

In some embodiments, once the Dig3 virtual oral appliance is generated in whatever iteration, a virtual 3D image is sent to be manufactured using conventional 3D printing, Carbon3D printing, hybrid manufacturing using 3D printing along with conventional suck down manufacturing with robotic insertions of sensors and/or hydrogels or other combinations of injection molding or other techniques. For example, in certain embodiments, the chemical composition for Dig1 portion can be stiffer in order to better hold onto the teeth and gums and be devoid of absorptive qualities, while the Dig2 portion can be made of a different chemical composition, which has absorptive qualities and can swell more easily. Useful chemical compositions comprise gels, hydrogels, polymer brushes, and other swellable chemicals. These can be mixed uniformly with one or more sensors and/or hydrogel, or alternately infused into Dig2 material after printing of Dig3.

In some embodiments, the computer program uses an axis graph with physical properties on one axis and chemical properties on the other. This data is used for manufacturing the device and, although holding different formulations will have chemical compatibility between them, such that when manufactured the formulations will seamlessly meld together as one piece, thus allowing the Dig3 oral appliance to be fabricated without the use of adhesives, glues, or mechanical locking devices. In some embodiments, the one or more sensors and/or hydrogel can be loaded and manufactured concurrently with the overall oral appliance. Alternatively, the sensor can be attached to the oral appliance by hand or machine. In some embodiments, the sensor can be attached to the interior and/or exterior of the device by an adhesive or the sensors can be disposed in discrete regions of the oral appliance in the cargo areas. In some embodiments, the sensor can have a soft polymer disposed about it. The polymer is soft to prevent damage of the sensor and the surrounding gums. In some embodiments, the polymer can be an electro conductive polymer that is disposed around or surrounds the sensor.

With this digital model, the oral appliance manufactured in accordance with Dig3 is now ready to be placed in the oral cavity of the patient either in a wet or dry form. The hydrogel portion of the Dig3 oral appliance is contracted when dry and will expand when wetted. It is the Dig2 portion of Dig3, which is the three-dimensional representation of the area to be detected which will monitor the diagnostic area in a three-dimensional manner once the oral appliance is inserted. For embodiments in which the one or more polymers used to make the oral appliance include a hydrogel, the hydrogel of the Dig3 oral appliance continuously samples along a diffusion gradient. This phenomenon is similar to a biologic wicking caused by the body tissues of the patient, which are at a lower diffusion gradient.

In various embodiments, the three-dimensional model has the hydrogel loaded and/or the sensor, the sensor web can be provided and the oral appliance can be made about the sensor, or sensor web.

Once the oral appliance is manufactured, the oral appliances are packed and shipped to a dental professional who will deliver them to the patient with instructions for their use. The patient then performs a single use assay and thereafter either downloads the information or sends the appliance to be analyzed. A new tray is used for each assay according to a prescribed regimen.

In some embodiments, oral appliances manufactured according to the three-dimensional model described herein can also be utilized to monitor periodontal or gum diseases. In gum disease the initial form of the gums is often reddened and swollen. As such, the gums are larger than normal. As they heal, the gums shrink back to their normal, healed state size and become pink and firm. In order to generate a Dig2 system to treat gum diseases, Dig2 can be modified to take into account the anticipated shrinking of the gums to insure that the detection layer is always in apposition to the diseased tissue. A sensor, for example a pressure sensor, can be positioned in the oral appliance adjacent this area and as the gums heal and shrink the pressure will decrease in this area. In some embodiments, if the gums are swollen by 2 mm, there can be a two week or 14 oral appliance detection period. The first oral appliance for use on the first day can have an initial Dig2 thickness of 0.6 mm identified as Dig2A. The second oral appliance, identified as Dig2B, can have a thickness of 0.7 mm and can be used by the patient on the second day. On the third day, the patient can use Dig2C oral appliance, which can have a thickness of 0.8 mm. The process repeats itself until day 14 when the thickness of Dig2N can be 2 mm, thus fully accounting for the shrinkage of the gums and also allowing the one or more sensors and/or hydrogel to always be in direct contact with the gums. If this approach were not followed, it could result in the patient having a gap between Dig2 and the gum and the resultant space would not allow for proper assaying. This is a progressive system, in which the Dig3 oral appliances are manufactured to account for daily and/or weekly changes to the topography of changing soft tissues. Thus, in certain embodiments, the thickness of surface oral appliance is incrementally configured for monitoring gum disease.

Figure 6A:
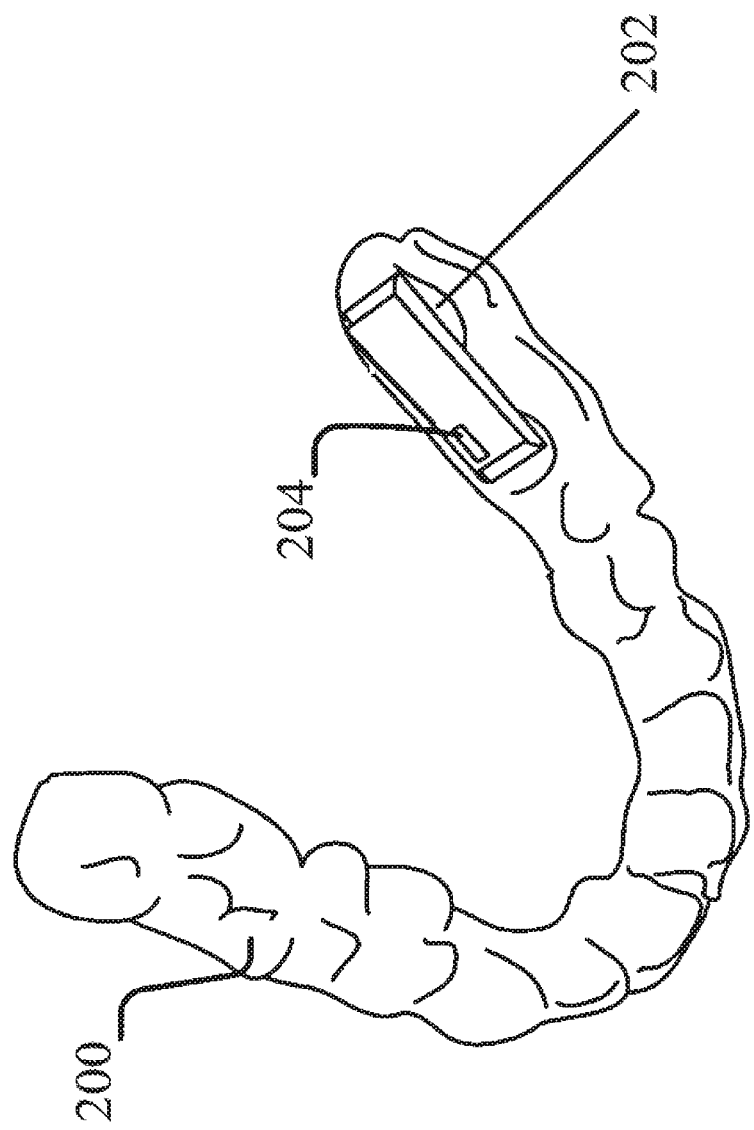
FIG. 6A schematically shows an embodiment of an oral appliance configured for application to the lower teeth and gums and a cargo area has a pressure sensor mounted either by hand or robotically on the outer surface of the oral appliance, which for example, can monitor pressure on a biting surface for teeth grinding (e.g., bruxism) or to assist in bite equilibration (adjusting one's bite).

FIG. 6A schematically shows an embodiment of an oral appliance 200 configured for application to the lower teeth and gums and a cargo area 202 that has a pressure sensor 204 mounted either by hand or robotically on the exterior surface of the oral appliance, which for example, can monitor pressure on a biting surface for teeth grinding (e.g., bruxism) and help in equilibrating a bite. The sensor will collect the data over a period of time. For example, over an evening period and the sensor will measure the biting or grinding habits of the patient over the evening period.

In other embodiments, the Dig3 oral appliance can be utilized as a diagnostic tool for testing of fluids in the oral cavity. In these embodiments, the hydrogel of the Dig3 oral appliance is absorptive both on its internal and external surfaces and can therefore be easily used to test the gingival crevicular fluids and/or saliva present in the oral cavity for diagnostic purposes. After the patient wears the Dig3 oral appliance, the oral appliance can be removed, placed into a container and then sent to a lab for analysis or in the case of sensors the information can be downloaded for analysis. The Dig3 oral appliance can test oral fluids over longer periods of time, and is thus significantly more effective than the fluid spot testing currently used in current technology. In some embodiments, the oral appliance can include absorptive material that can retain the sample (e.g., cells, fluid (e.g., blood, saliva), etc.). Such material includes, but is not limited to, absorptive hydrogels, absorptive sponge, or sponge-like material, polyvinyl acetate (PVA), polyurethane (PU), cellulose, polyester, rayon, cotton, and/or a combination thereof.

Figure 6B:
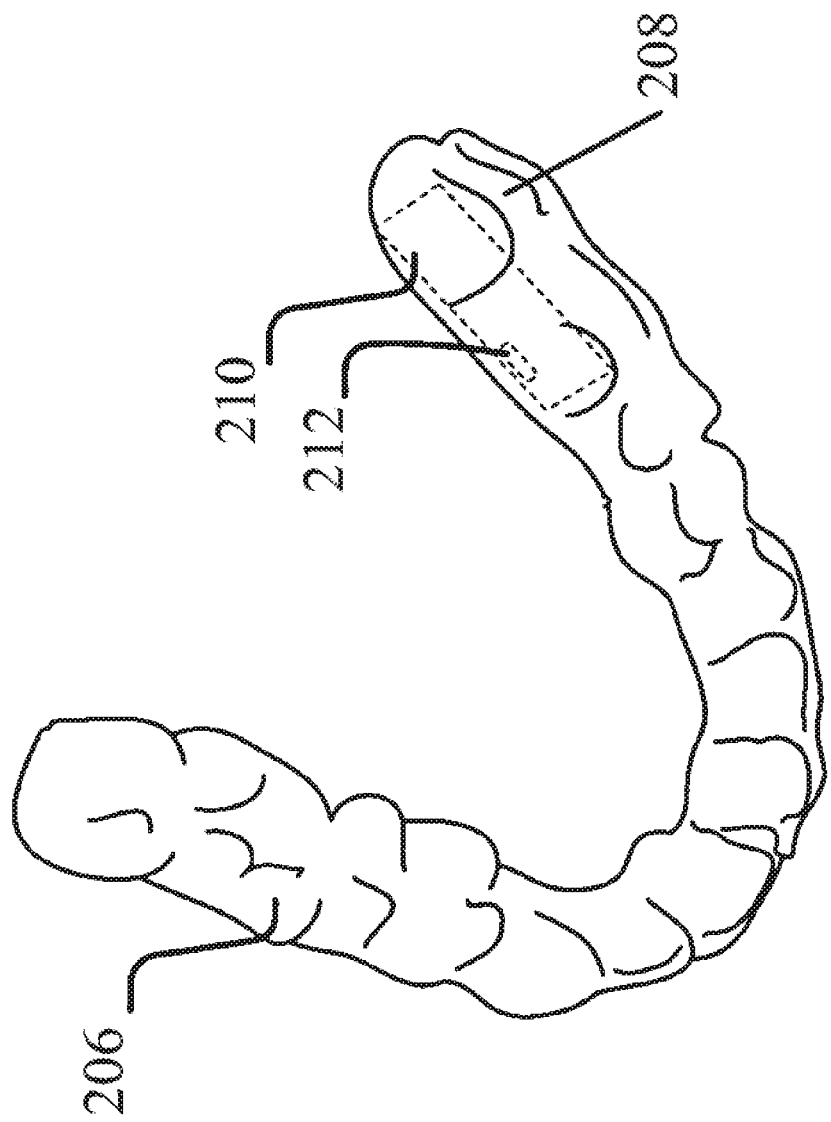
FIG. 6B schematically shows an embodiment of an oral appliance configured for application to the lower teeth and gums and a cargo area that has a hydrogel disposed either by hand or robotically on the interior surface of the oral appliance, which for example, can collect cells, for example, from the sulcus for culture and sensitivity testing. The hydrogel can have a tab for easy removal of the hydrogel, or the whole tray can then be sent to the lab for further testing.

FIG. 6B schematically shows an embodiment of an oral appliance 206 configured for application to the lower teeth and gums and a cargo area 208 that has a hydrogel 210 disposed either by hand or robotically on the interior surface of the oral appliance, which for example, can collect cells, for example, from a cancerous site. The hydrogel can have a tab 212 for easy removal of the hydrogel, which can then be sent to the lab for further testing. The hydrogel can be placed at discrete positions in the oral appliance to collect tissue samples, saliva, blood, bacteria or other material and then sent to the lab for analysis.

The dimensions of the oral appliance, among other things, will depend on the target detection site. The oral appliance can be adapted to any size and shaped to receive at least a portion of the teeth and/or soft tissue areas inside the mouth. For example, the oral appliance is designed to contour, support, and hold the polymer gel material and, in various embodiments, extends to at least the muco-gingival junction, or at least 2 mm to 5 mm buccally or lingually beyond a gingival margin, or contact all or substantially all of one or more teeth and/or soft tissue areas inside the mouth and adjacent buccal and lingual soft tissue areas.

In various embodiments, the oral appliance has a thickness of from about 0.06 inches to about 0.2 inches, a depth of at least about 1 mm to about 5 mm, and a width of from about 1 mm to about 10 mm. In certain embodiments, the thickness of the oral appliance is incrementally configured for monitoring a gum disease.

Materials of Oral Appliance

The material of the oral appliance can be any material that can hold one or more sensors and/or hydrogel or in some embodiments, retain a sample (e.g., blood, saliva, cells, etc.). In various embodiments, the material from which the oral appliance can be manufactured includes swellable polymer materials, such as, for example gels, hydrogels, polymer brushes or combinations thereof.

In various embodiments, polymer gels, hydrogels, and brush polymers can be formulated to have varying degrees of swelling ability. Thus, a treatment that involves the application of pressure to soft tissues of the mouth can be accommodated through the specific formulation of Dig2 materials to incorporate the desired amount or percentage of swelling during treatment. In some embodiments, the polymer comprises 20 wt % to 90 wt % of the formulation.

In various embodiments, the molecular weight of the gel can be varied as desired. The choice of method to vary molecular weight is typically determined by the composition of the gel (e.g., polymer, versus non-polymer). For example, in various embodiments, when the gel comprises one or more polymers, the degree of polymerization can be controlled by varying the amount of polymer initiators (e.g., benzoyl peroxide), organic solvents or activator (e.g., DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000 g/mol.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different molecular weights, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, when the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. In other embodiments, the hydrogel material can hold collected biological materials when the hydrogel material is hypo-saturated, saturated, or supersaturated. There are many advantages resulting from using hydrogel in making the oral appliances described herein. Generally, hydrogel materials provide an effective contact medium for gum compression and for collecting biological materials for diagnosis. The above can hold the sample (e.g., saliva, blood, cells, etc.) when the oral appliance is removed and then the oral appliance can be sent to the lab for testing. Sending out the entire oral appliance to the lab can prevent cross contamination of the patient's hands contaminating the sample collected by the hydrogel. In some embodiments, only the hydrogel can be removed and then sent out to the lab for testing.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (for example, PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, also useful material for preparing the oral appliances described in this disclosure comprise reactive segmented block copolymers containing hydrophilic domain(s) and showing good surface properties when the block copolymer is covalently bound to substrates containing complimentary functionality. The hydrophilic domain(s) will comprise at least one hydrophilic monomer, such as, HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof. Still further examples are the hydrophilic vinyl carbonate or vinyl carbamate monomers. Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl(meth)acrylate, poly(ethylene glycol(meth)acrylate), tetrahydrofurfuryl(meth)acrylate, (meth)acrylamide, N,N'-dimethylmethacrylamide, N,N'-dimethylacrylamide("DMA"), N-vinyl-2-pyrrolidone (or other N-vinyl lactams), N-vinyl acetamide, and combinations thereof. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process.

The polymer gel material can comprise orally soluble or insoluble polymers. For example, the polymer gel material may be designed to be insoluble in the oral environment, yet still release the medicament that is coated on or internally imbedded in the polymer gel material. Various polymers whether soluble, insoluble, semi-soluble or combinations of these may be used to create a polymer gel material with specific activities suitable for assaying. Many plastics and plastic combinations are suitable for this application. A few examples of possible plastics include: polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters, urea-formaldehyde, or any like plastics.

In one embodiment, the hydrogel material may comprise a backing material (e.g., a closed cell plastic backing material) to minimize collection of the biological material by the oral appliance. The hydrogel material can be constructed to increase collection of the biological material to receive a bolus collection or the polymer gel material may be designed to prevent biological material from spilling out of the hydrogel material and allow the biological material to pass through the polymer gel hydrogel over time to obtain a sustained collection profile. In other words, in various embodiments, the hydrogel material may have an internal structural spacing sized relative to the viscosity of the biological material to absorb and allow the biological material to pass therethrough to achieve the desired collection profile, for example, immediate collection, bolus collection, and/or sustained or controlled collection.

In some embodiments, the dimensions of the polymer material (e.g., gel, hydrogel, etc.), among other things, will depend on the target diagnosis site and whether local or systemic collection of the biological material is required as well as the type of biological material collection profile to achieve. In some embodiments, the oral appliance is prepared primarily of polymer material and can be adapted to any size and shape required to receive at least a portion of the teeth and/or soft tissue areas inside the mouth to collect the biological material. For example, the polymer material may, in various embodiments, extend to at least the mucogingival junction, or at least 2 mm to 5 mm buccally or lingually beyond a gingival margin, or contact all or substantially all of one or more teeth and/or soft tissue areas inside the mouth and adjacent buccal and lingual soft tissue areas. In various embodiments, the polymer material contacts all or substantially all of one or more teeth and/or soft tissue areas inside the mouth. In various embodiments, the polymer material contacts the soft tissue and teeth at or near a gingival margin or sulcus. In various embodiments, the polymer material has a thickness of from about 0.06 inches to about 0.2 inches, a depth of at least about 1 mm to about 5 mm and a width of from about 1 mm to about 10 mm.

Computer Implemented System

In various embodiments, the present disclosure provides a computer implemented method of making an oral appliance. The method comprises creating a digital record of a patient's oral cavity, the Base Image (BI), by obtaining a digital image of at least a portion of the teeth, and/or soft tissue of the oral cavity by using an imaging device. The BI is overlaid to create a first digital image, Dig1. Subsequently, a second digital image, Dig2, comprising at least a portion of the teeth and/or soft tissue of the oral cavity in need of a sensor is additively or subtractively generated. Thereafter, the first digital image, Dig1, and the second digital image, Dig2, are combined to form a third digital image, Dig3, of the oral cavity treatment area and the third digital image is then stored in the computer and used for manufacture.

In some embodiments, there is a computer implemented method of producing an oral appliance pre-loaded with at least one or more sensors and/or hydrogel using a computer, comprising: using the BI of the digital image of the patient's mouth, generating first digital data representing an overlay of at least a portion of the teeth and/or soft tissues areas of the oral cavity of a patient, generating second digital data by performing a specified three dimensional addition of at least a portion of the teeth and/or soft tissues areas of the oral cavity to determine discrete regions of the oral cavity in need of treatment, combining the first digital data and the second digital data to form third digital data, from which the oral appliance can be produced, wherein the third digital data comprises positions for at least one or more sensors and/or hydrogel to be placed at the discrete regions in the oral cavity in need of diagnosis.

In other embodiments, a computer-implemented method is provided for diagnosing a condition of the teeth and/or soft tissue areas inside the oral cavity. The computer-implemented method comprises generating a first digital data, Dig1, representing at least a portion of the teeth and/or soft tissues areas of the oral cavity of a patient from the BI. Subsequently, a second digital data, Dig2, is generated by performing via the computer a digital segmentation of at least a portion of the teeth and/or soft tissues areas of the oral cavity comprising discrete regions of the oral cavity in need of treatment. The first digital data, Dig1, and the second digital data, Dig2, are then combined via computer to form the third digital data, Dig3, from which the oral appliance can be produced, wherein the oral appliance has at least one or more sensors and/or hydrogel positioned at the discrete regions requiring diagnosis in the oral cavity.

In various embodiments, a computer based system further comprises creating a virtual 3D image of the oral appliance indicating the discrete regions requiring diagnosis in the oral cavity; displaying on a display the virtual 3D image and performing interactive diagnosis. Imaging devices utilized to generate the various digital data sets include, without limitations, a digital camera, X-ray device, hand-held 3-D scanner, laser scanner, computerized tomography (CT) scanner, magnetic resonance imaging (MRI) scanner, coordinate measuring machine, destructive scanner or ultrasound scanner, generating first digital data, Dig1, representing at least a portion of the teeth and/or soft tissues areas of the oral cavity of a patient based on an imaging device image (BI), generating second digital data, Dig2, by performing via the computer a digital segmentation of at least a portion of the teeth and/or soft tissues areas of the oral cavity comprising discrete regions of the oral cavity in need of treatment, combining via the computer the first digital data, Dig1, and the second digital data, Dig2, to form third digital data, Dig3, from which the oral appliance can be produced having at least one or more sensors and/or hydrogel positioned at the discrete regions requiring diagnosis in the oral cavity.

In other embodiments, the three-dimensional representation of the third digital data, Dig3, is stored in a format suitable for use by a manufacturer to produce the oral appliance pre-loaded with at least one or more sensors and/or hydrogel at areas targeted for diagnosis. Manufacturing comprises a first chemical composition according to the first digital data, Dig1, and a second chemical composition according to the second digital data, Dig2. The two combined chemically merge and represent the image of the third digital data, Dig3. At least one of the chemical compositions includes one or more sensors and/or hydrogel while the other can be a polymer gel, brush polymer, another absorptive material or combinations thereof.

Figure 7:
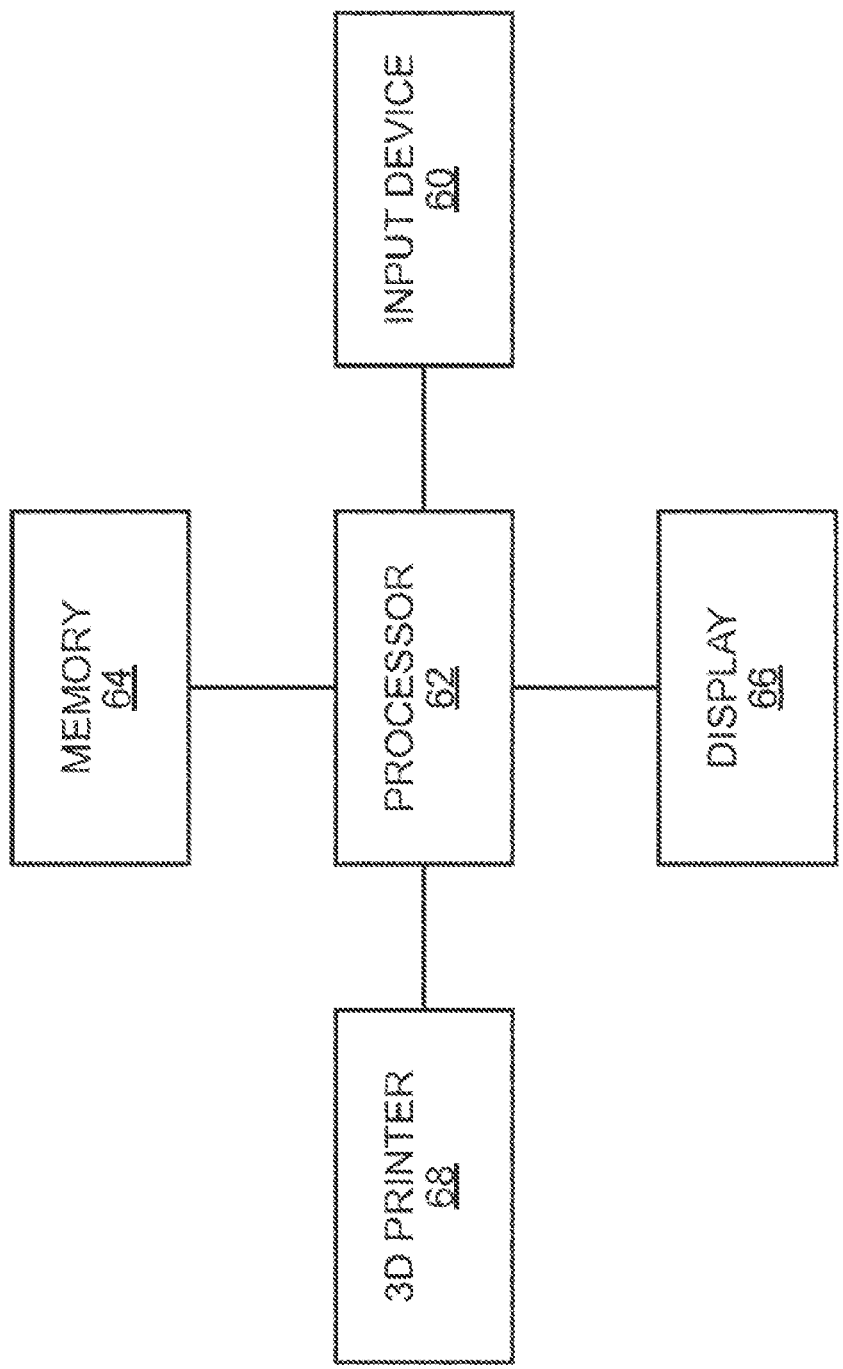
FIG. 7 is a block diagram of an embodiment of a computer-implemented system for producing an oral appliance for measuring chemical, physical, and environmental parameters.

Referring to FIG. 7, it illustrates an embodiment of the computer-implemented system for producing an oral appliance. An input device or scanner 60 is used to scan the oral cavity of and thus generate a digital record of the patient's mouth (BI). The scanner can be an MRI scanner, a CT scanner, a PET scanner, a digital scanner, an X-Ray machine, or an intra-oral scanner, for example. In various embodiments, scanner 60 can scan the patient's teeth, soft tissue, or both to obtain a digital data set of the teeth and/or soft tissue areas inside the mouth from which is generated the BI. The digital data can be stored in a database, such as for example a computer that has a processor 62, which sends the digital data to its memory 64 and/or can display it in a virtual 3D image display 66 of processor 62. The database and/or processor can comprise an input device (e.g., keyboard, touch screen, voice activation, etc.) to allow a user to enter, display, edit, and/or transmit on or more images from Dig1, Dig2, Dig3. The processor 62 comprises logic to execute one or more instructions to carry instructions of the computer system (e.g., transmit instructions to the 3D printer, etc.). The logic for executing instructions may be encoded in one or more tangible media for execution by the processor 62. For example, the processor 62 may execute codes stored in a computer-readable medium such as memory 64. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium.

Based on memory 64, processor 62 can generate Dig2 and Dig3 and thereafter send a 3D image to the 3D printer 68 of a stereolithography apparatus.

In various embodiments, an authorized user can input, edit data and approve or prescribe a treatment plan based on the virtual 3D images displayed at the user interface of the computer processor 62 and/or another treating computer networked with computer processor 62. Although the components of the system of FIG. 7 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc.).

The user can interface with the computer via a user interface that may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of a user with the system via user interface. The user interface may be directly coupled to database or directly coupled to a network server system via the Internet or cloud computing. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (e.g., network/stand-alone computers, personal digital assistants (PDAs), WebTV (or other Internet-only) terminals, set-top boxes, cellular/phones, screenphones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (e.g., the Internet).

The database can be stored in storage devices or systems (e.g., Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into centralized database, a tracking component for tracking information received and entered, a search component to search information in the database or other databases, a receiving component to receive a specific query from a user interface, and an accessing component to access centralized database. The receiving component is programmed for receiving a specific query from one of a plurality of users. The database may also include a processing component for searching and processing received queries against data storage device containing a variety of information collected by collection device.

The disclosed system may, in some embodiments, be a computer network based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). In accordance with one embodiment, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., 3D printers, printer heads, etc.).

In accordance with one embodiment of the present application, the data may be downloaded in one or more textual/graphical formats (e.g., RTF, PDF, TIFF, JPEG, STL, XML, XDFL, TXT etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view viewing the search results and underlying documents at the user interface, which allows viewing of one or more documents on the same display.

In various embodiments, the computer software can create a 2D or 3D digital image of the patient's oral cavity to allow the treatment provider to review and discuss the proposed treatment with the patient. In another embodiment, the software can process the scanned data and provide the user/operator with useful data including tooth measurements (e.g. arch width, arch length, tooth size, angulations, sulcus size, etc.) to assist the user in fine-tuning the assay plan. The computer can then provide the operator with options in staging the assay plan from one stage to another stage, or it can completely generate all stages ranging from the initial to final desired stage. The staging can be done automatically.

Figure 8:
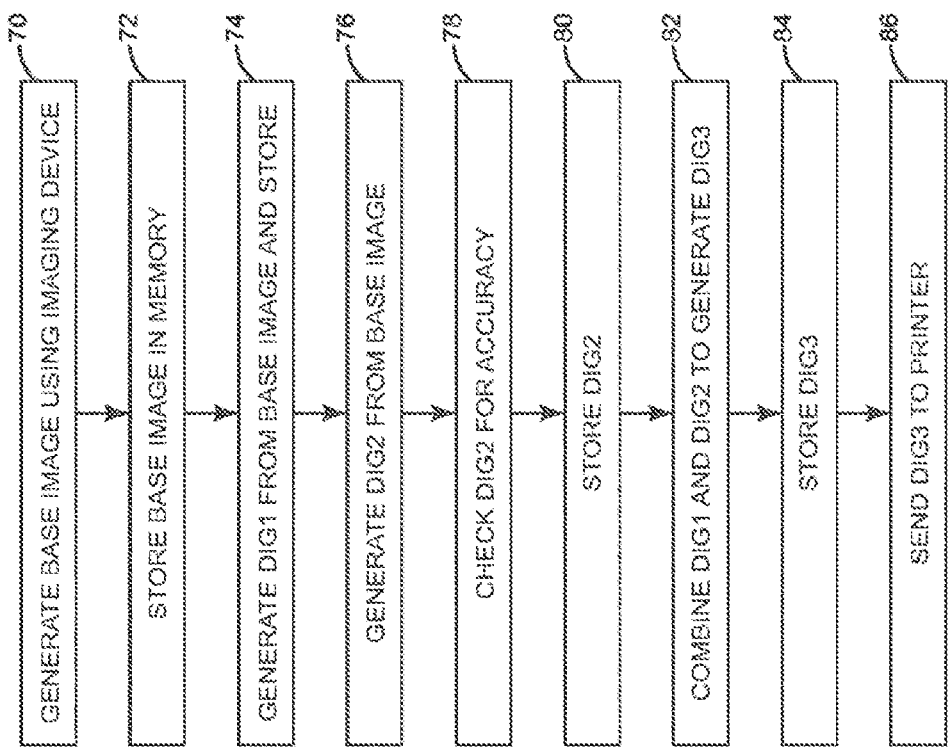
FIG. 8 is a flow chart illustrating an embodiment of the computer-implemented system for producing an oral appliance for performing oral cavity chemical, physical, and environmental measurements including cell or saliva sampling.

FIG. 8 is a flow chart illustrating the logic steps followed by processor 62 of FIG. 7. The first step 70 comprises generating a Base Image (BI) of at least a portion of the teeth and/or soft tissues by using an imaging device. In step 72, the BI is stored in the memory of the processor. In step 74, a first data set (Dig1) is generated by the computer layering over the BI of at least a portion of the teeth and/or soft tissues. The Dig1 is stored.

In step 76, a second data set (Dig2) is generated by digitally adding a specific three dimensional layer over at least a portion of the teeth and/or soft tissues from the Base Image.

Thereafter, in step 78, the processor can decide if all discrete regions of the oral cavity in need of assay have been identified or if they have not been, then the digital segmentation step will occur again. Dig2 will also be checked for accuracy.

If all the desired discrete regions have been identified, then in step 80, the processor stores the data, which includes the discrete regions in need of assay as a separate set corresponding to Dig2. The first and second data sets are combined in step 82 to generate a third data set corresponding to Dig3. The third data set is stored in step 84 and then sent to a 3D printer in step 86.

Figure 9A:
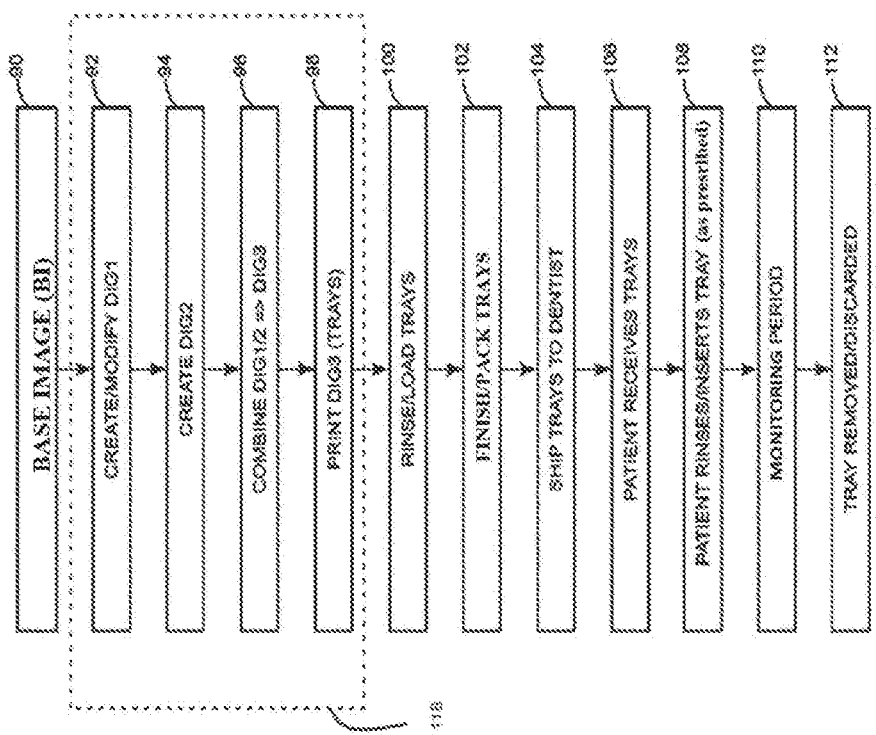
FIG. 9A is a flow chart illustrating an embodiment of the computer-implemented system to generate and manufacture an oral appliance and use of the oral appliance by a patient.

FIG. 9A is a flow chart illustrating an embodiment of the computer-implemented system for assaying a patient utilizing an oral appliance produced according to this disclosure. As described above, the oral cavity of the patient is scanned or a mold can be scanned in step 90. Based on the information gathered in step 90, Dig1 is generated in step 92. Subsequently, a second digital data set is generated and Dig2 is obtained in step 94. As discussed above, Dig1 and Dig2 digital data sets are combined, in particular Dig2 is subtracted from Dig2, in step 96 to generate Dig3, which provides the logic and instructions to manufacture Dig3 in step 98. A group of steps 118, i.e., steps 92 through 98, is optionally replaced by operations detailed below in accordance with the group of steps 119 shown in FIG. 9B with relation to further embodiments of the present disclosure.

Figure 9B:
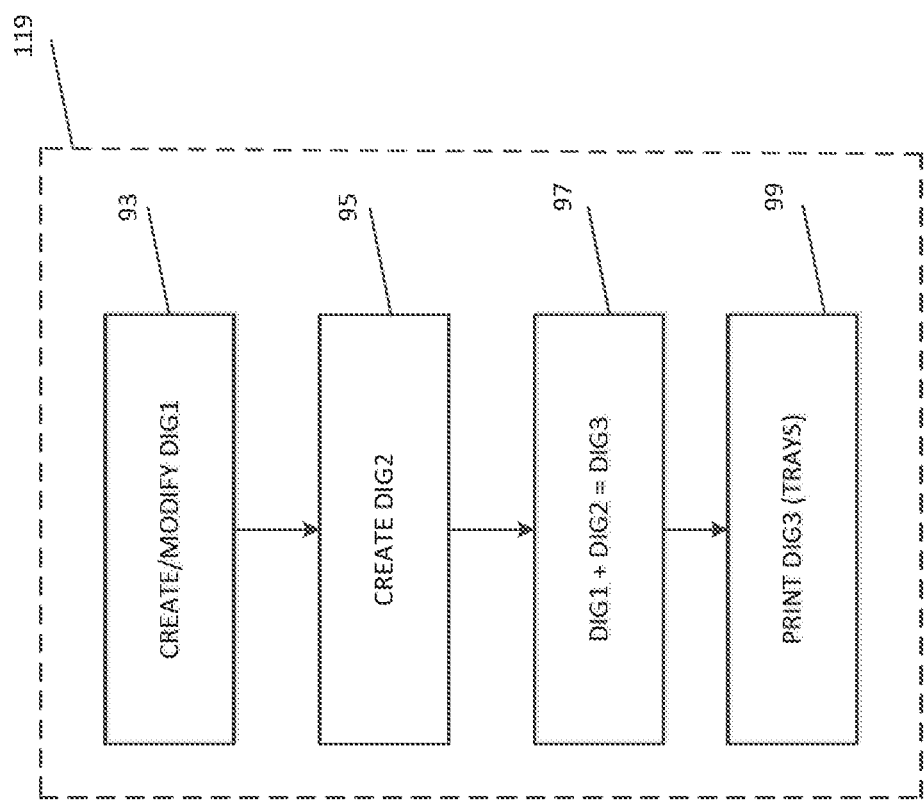
FIG. 9B is a flow chart illustrating an embodiment of the computer-implemented system to generate and manufacture an oral appliance and use of the oral appliance by a patient.

FIG. 9B is a flow chart illustrating an embodiment of the computer-implemented system for assaying a patient utilizing an oral appliance produced according to this disclosure. Based on the information gathered in step 90, Dig1 is generated in step 93. Subsequently, a second digital data set is generated and Dig2 is obtained in step 95. As discussed above, Dig1 and Dig2 digital data sets are combined, and in this particular embodiment Dig2 is added to Dig1, in step 97 to generate Dig3, which provides the logic and instructions to manufacture Dig3 in step 99.

Following step 98 the oral appliances produced by a stereolithography, or extrusion type 3D printing, are then rinsed and loaded with one or more sensors in step 100. The oral appliances are then dried and packed in step 102 and shipped to a dental professional in step 104. Alternatively, there may be no rinse step or sensors and/or hydrogel loading as the stereolithography machine may have the one or more sensors and/or hydrogel may have already been loaded. In step 106, the patient receives the oral appliances and inserts them as required in a daily process in step 108. After the monitoring period of step 110 is completed, each oral appliance is removed and analyzed in step 112 or the hydrogel insert is removed by the patient and the hydrogel is sent to the laboratory for analysis. Alternatively, if a diagnosis needs to be made, the oral appliances can be sent to a laboratory for testing and then the oral appliances disposed of by the laboratory.

Stereolithography

Stereolithography is the manufacturing process that may be employed for rapidly and accurately producing the oral appliances described herein. A commercially-available stereolithography apparatus (SLA) may be employed to carry out the rapid prototyping methods described herein. In many cases, stereolithography is carried out using a defined amount of liquid UV-curable photopolymer, which can be a "resin" and an ultraviolet (UV) laser to assemble all or a portion of the oral appliance one layer at a time. According to such methods, the laser beam will "trace" a cross-sectional pattern, for each layer of the oral appliance, on the surface of the liquid resin. By exposing the resin to UV energy, the resin solidifies (or "cures") in accordance with the pattern traced by the beam of energy, which adheres to the layer beneath it.

After a pattern has been traced by the beam of UV energy, a so-called elevator platform within the SLA descends by a single layer thickness, typically about 0.05 mm to 0.15. Next, a resin-filled blade traverses across each part of the cross-section, which re-coats the model with new UV-curable resin. On this new layer of resin, the subsequent layer pattern is traced, adhering to the previous layer. This process allows for a complete three-dimensional, real-sized prototyped oral appliance to be produced. After a prototype oral appliance is produced, the oral appliance may, optionally, be cleaned and the excess resin removed therefrom by immersion in a chemical bath and then cured in a UV oven. U.S. Pat. No. 4,575,330 ("Apparatus for Production of Three-Dimensional Objects by Stereolithography") provides a non-limiting method of stereolithography, which may be used in the present application and is hereby incorporated by reference in its entirety. With respect to the oral appliance described herein, the print heads of the SLA can dispense polymers according to instructions provided by Dig1 and Dig2 to generate Dig3 as described above. Accordingly, the viscosity of the polymer, curing rates, feed rates to the print heads can be considered in manufacturing the oral appliances described herein.

An alternate method of stereolithography involves the deposition of successive layers of liquid or powder onto a hard surface, with each layer immediately cured by a beam of UV energy, and in this way builds up the oral appliance from a series of cross sectional patterns of Dig3. These layers, which correspond to the virtual cross section of Dig3, are joined together or fused automatically to create the oral appliance. Further, it will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Control System, Apparatus and Method

A further embodiment of the present disclosure varies the aforesaid embodiments to effect design and construction of an oral appliance which is directed to improved diagnostic area dynamics. Unless otherwise stated, this embodiment incorporates the features discussed above except as further modified herein. In particular, the base image (BI) previously discussed is used to construct an oral appliance which is to be used to monitor areas in the oral cavity with control of contact pressure applied to a diagnostic area, which includes any or all of teeth and tissues discussed above, and/or areas surrounding the treatment area.

Any of the various forming techniques discussed above are optionally used to manufacture the oral appliance. Forming techniques for the oral appliance may be categorized into three groups. Extrusion type 3D printing wherein print heads successively extrude layers of melted materials to produce the oral appliance. Alternatively, instead of using melted material, UV curable materials may be used wherein print heads eject the UV curable materials which once ejected are exposed to UV rays which cure them in place. Similarly, materials may be ejected which are cured by other means such as exposure to oxygen or infrared rays. Depending on the characteristics of the materials to be used, e.g., some materials may not be suitable for thermoforming wherein they are melted and allowed to solidify. Extrusion type 3D printing will be hereinafter considered to apply to types of printing wherein a material is ejected and subsequently cured by any method. Photopolymerization 3D printing, also termed stereolithography (SLA) as discussed above, is a process wherein a vat of liquid polymer which is cured by exposure light is acted upon by light rays to cure selected portions of the liquid polymer, photopolymer, in successive layers to form the oral appliance. Recent developments in photopolymerization 3D printing have resulted in the use of graphene materials which provide a very rigid structure, e.g., a structure having a high modulus of elasticity. Graphene material is optionally used in any embodiments described herein where such a structural characteristic is required or desirable.

It is noted that in the above discussion the term "stereolithography" has been occasionally applied herein to both photopolymerization methods wherein an object is produced using a vat of liquid polymer and extrusion type 3D printing because it generally it relates a method of producing 3D objects. As will be appreciated by those skilled in the art, where multiple print heads and materials are involved, the above discussion is relating extrusion type 3D printing.

Additionally, a vacuum forming hybrid method is optionally used wherein a carrier is formed from a sheet of thermoformable material by vacuum molding the sheet over a 3D model of the base image BI or a modified version thereof as will be discussed below. Further materials are added to the formed sheet using any or all of 3D printing, robotic application of material, or immersion in a solution containing hydrogel.

Figure 10A:
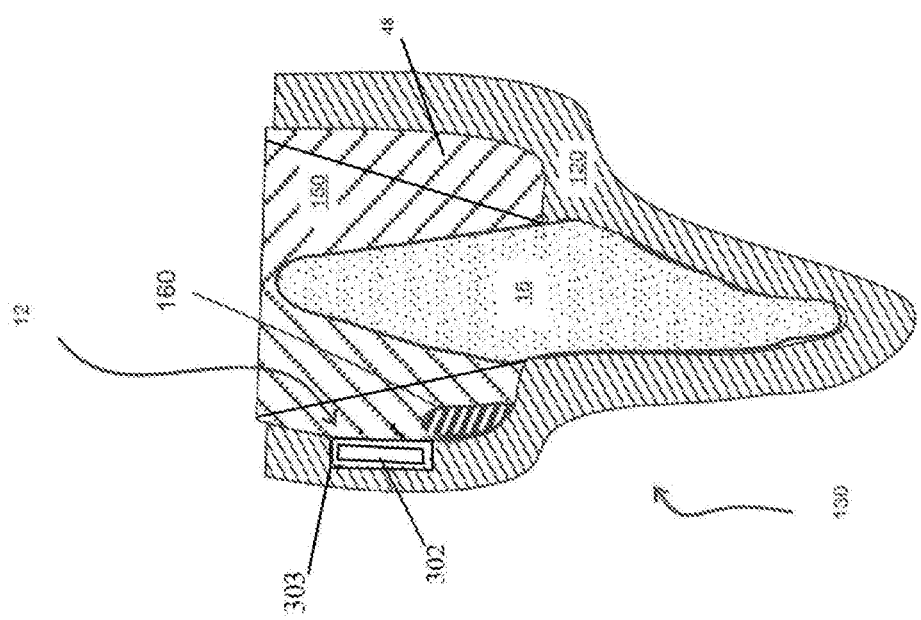
FIG. 10A is a cross-sectional view of an area of the oral appliance of FIG. 1 taken along line IXa-IXa, at an area of interest housing a sensor that monitors physical, chemical, biological, and/or environmental information associated with the oral cavity at a sulcus area.

Referring to FIG. 10A, a cross section of an oral appliance 130 formed of a platform carrier shell 120, which includes a data collection device 302 (e.g., sensor) that monitors physical, chemical, biological, and/or environmental information associated with the oral cavity, is shown. The data collection device (e.g., sensor) is disposed in a cargo area 303, which is a space in the oral appliance that corresponds to the virtual image of Dig2 and is added onto or subtracted from the virtual image of Dig1 and made in the device when it is manufactured using virtual image Dig3. In some embodiments, the oral appliance can be printed using Carbon3D technology by operation parameters for the continuous production of the oral appliance using 3D printing technology as described in US Publication No. 20150097315 having Ser. No. 14/569,202 filed Dec. 12, 2014. The entire disclosure of this patent publication is herein incorporated by reference into the present disclosure. In some embodiments, the cargo area 303 can be filled with an electroconductive medical polymer 301 that includes microparticles and/or nanoparticles as discussed below that conduct electricity to and from the sensor.

The view of the oral appliance 130 in FIG. 10A corresponds to a view of the oral appliance taken along line IXa-IXa of the oral appliance 10 of FIG. 1. The carrier shell 120 is illustrated disposed on the upper tooth 16 and associated tissue 150 (e.g., gingival tissue) of a patient in order to show that the carrier shell tightly conforms to the underlying oral structure. For the purpose of simplicity, the associated tissue 150 is shown as homogeneous. However, it is to be understood that the associated tissue 150 may include both soft tissue, e.g., gums, and bone, and the extent of the oral appliance 130 is not to be considered limited to such coverage of the structure of the oral cavity. A diagnostic area 160 of the associated tissue 150 is shown which is in need of monitoring. The diagnostic area, for example, can be gingival cells where cancerous cells were removed or it may be an area of periodontal disease that requires monitoring of saliva in which the saliva will weakly conduct electricity to the sensor. If there is too little saliva or bacteria increase in the area, this may interfere with the conduction of the electricity to the sensor and it will send a signal to the processor external to the oral appliance, where it will be stored and an alert will be generated to the wearer and/or the health care provider as the conductivity will be too low. The data collection device 302 is disposed in a cargo area 303 adjacent to the teeth and contacts the soft tissue of the oral cavity in this embodiment.

In some embodiments, the sensor is configured to detect any suitable marker or trigger in the saliva, mucosal fluids, crevicular fluids or air of the oral cavity. The trigger may be a negative or positive indicator of oral hygiene or oral conditions. Examples of suitable markers/triggers include pH, molecules, proteins, organisms, oral activities such as triclosan, or the like. More specifically, suitable markers include phosphates, amino acids, potassium salts, or stannous salts. In some embodiments, the sensor is configured to detect a particular pH or range of pH.

In some embodiments, the sensor can be a pH sensor taking intraoral pH and plaque pH. It is known that acidic fermentation products produced by plaque microorganisms in the presence of sugar and carbohydrates are strongly associated with dental caries. Because of the importance of plaque pH, measurement of plaque pH is now widely accepted as a method of evaluating the effect of carbohydrates on oral health. In some embodiments, caries is indicated by low saliva pH, local pH (e.g., at specific locations on the hard tissue) and by acid-producing oral bacteria (specifically *Lactobacillus* species, *Streptococcus mutans*, and *Actinomyces* species), where the sensor can detect such low pH.

In some embodiments, the oral conditions identified by the devices described herein include, but are not limited to, conditions associated with poor oral care, conditions which may be diagnosed by examination of the oral cavity, and systemic conditions which have been recognized or otherwise identified by the American Dental Association to be correlated with poor oral care.

Oral diseases suitable for detection include caries, gingivitis, periodontitis, halitosis, fungal infections and dry mouth. Gingivitis may be indicated by the markers IL-1β, PGE2, arginine and Gingipains. Gingivitis may also be indicated by elevated levels of one or more of *P. gingivalis, C. gingivalis, P. melaminogenica, Treponema denticola, Bacterioides forsythus* and *S. mitis*. Halitosis may be indicated by volatile sulfur compounds, including methyl mercaptan, dimethylsulfide and hydrogen sulfide. Periodontitis may be indicated by elastases, dipeptidylpeptidase, β-glucuronidase, lactoferrin, platelet-activating factor (PAF), ICPT (pyridinoline cross-linked carboxyterminal telopeptide), cathepsin B (a cysteine protease), cystatins, MMP-1, collagenase-2 (matrix metalloproteinase, MMP-8), MMP-13 (collagenase-3), gelatinase (MMP-9), hydroxyl-deoxyguanosine and immunoglobulins such as IgA, IgG and IgM. Bone-related biomarkers from oral fluids associated with periodontal diseases also include calprotectin, osteocalcin, ostenocetin and osteopontin.

Caries may be indicated by low saliva pH, local pH (e.g., at specific locations on the hard tissue) and by acid-producing oral bacteria (specifically *Lactobacillus* species, *Streptococcus mutans*, and *Actinomyces* species). A few non-oral based systemic diseases that are also indicative with oral malodor are: fetor hepaticus, an example of a rare type of bad breath caused by chronic liver failure; upper and lower respiratory tract infections utilizing phlegm and sputum (sinus, bronchial and lung infections); renal infections and renal failure; and trimethylaminuria ("fish odor syndrome") (Tangerman A. Halitosis in medicine: a review. Int Dent J. 2002 June; 52 Suppl. 3:201-6), which is incorporated by reference herein in its entirety. High concentrations of acetone (known as "acetone breath") in breath can indicate diabetic ketoacidosis.

In some embodiments, the pH sensor can detect unwanted levels from tooth whitening compositions. For example, the pH of different whitening products ranges from 3.67 (highly acidic) to 11.13 (highly basic). The dentist-supervised home-bleaching products have a mean pH of 6.48 (range 5.66 to 7.35). The over-the-counter whitening products have a mean pH of 8.22 (range 5.09 to 11.13), and the whitening toothpastes have a mean pH of 6.83 (range 4.22 to 8.35). The pH sensor can detect these ranges and ranges above or below these ranges. This will cause the system to record the pH data and if a range is reached that is above or below the set range, the system will send an alert notifying the user or healthcare practitioner. In this way, the oral appliance can monitor the delivery of medicaments (e.g., drugs, bleaching products, etc.) to the oral cavity.

FIG. 10B shows the platform carrier shell 120 absent the tooth and associated tissue 150. The platform carrier 120 corresponds to the virtual oral appliance defined by the digital image Dig1, which corresponds to a substantially uniform layer disposed over the base image BI so as to conform to the oral structure. Hence, theoretically, when the platform carrier 120 is situated as shown in FIG. 10A, the pressure exerted on the diagnostic area is negligible as no deflection of the platform carrier 120 is needed to fit on the underlying oral cavity structure. In many situations this is desirable as the diagnostic area 160 may be highly sensitive to pressure. Additionally, such a configuration is desirable when there are no specific diagnostic areas and the platform carrier is provided with the apparatus 300 to be generally disposed in the oral cavity. In such instances, the platform carrier 130 is formed of any of the aforesaid materials that are suitable for harboring the apparatus 300. In this case, the oral appliance 130 is formed by any of extrusion 3D printing, photopolymerization 3D printing, vacuum forming over a 3D printed mold of the oral cavity formed using the base image BI, a combination of any or all of these techniques, and/or the like.

As noted above, the oral appliance 130 may be used to apply the apparatus 300, which may include one or more sensors and/or hydrogel, and exert negligible pressure to the underlying oral cavity structure. However, there are situations wherein enhanced contact with certain regions of the oral cavity structure is desirable. As would be expected of the substantially contact pressureless fit of the oral appliance 130, motion of the jaw and tongue can result in the oral appliance losing contact at areas of the oral cavity structure, which will result in loss of the intimate contact of the one or more sensors and/or hydrogel in the oral appliance 130 with an area of intended diagnosis, such as the diagnostic area 160 and a resultant loss of transferal of the information from the area to be diagnosed. Furthermore, loss of contact with the underlying oral structure allows saliva or ingested beverages to circulate between the oral appliance and the area to be diagnosed resulting in some of the information to be lost and/or corrupted. Thus, in some situations it is desirable to modify the oral appliance 130 to increase contact pressure with the area to be diagnosed in order to maintain contact with the diagnostic area. Additionally, it may also be desirable to increase contact pressure with areas surrounding the area to be diagnosed in order to better exclude liquids, such as saliva or beverages, from the surface of the oral appliance 130 in contact with the area to be diagnosed. The data collection device 302 is disposed in a cargo area 303 adjacent to the teeth and contacts the soft tissue of the oral cavity in this embodiment.

Figure 10C:
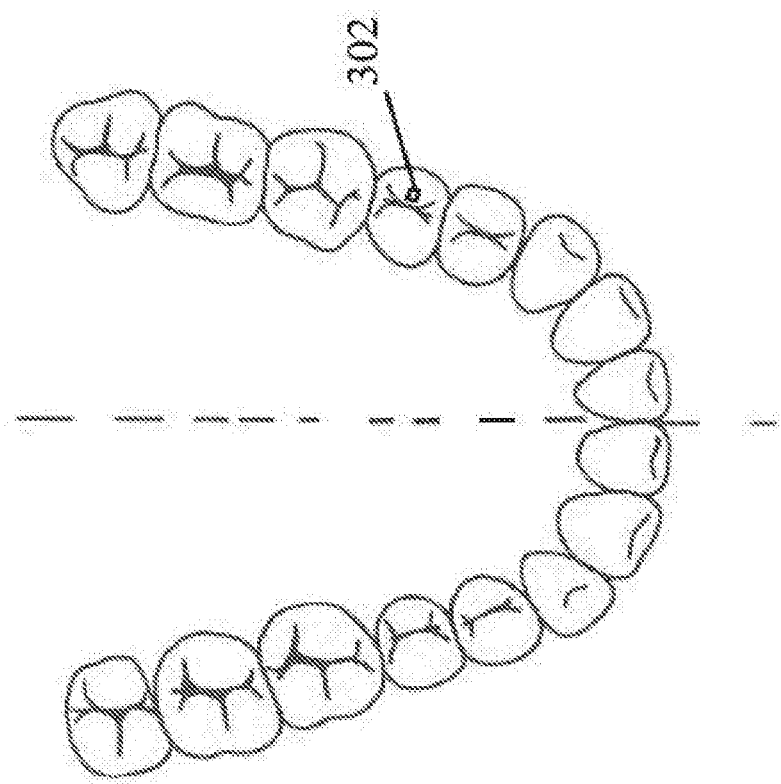
FIG. 10C is a top view of the oral appliance of FIG. 1 depicted in a simplified manner lacking intricate detail for simplicity of viewing, indicating various components of the apparatus that monitors physical, chemical, biological, and/or environmental information associated with the oral cavity (dashed line outlined) disposed at the bottom of positions for alignment adjacent bottoms of top molars, sensors positioned in indentations of the interior surface of the oral appliance for measurements of properties adjacent teeth, and sensors positioned in indentations of the exterior surface of the oral appliance. For example, the data collection device 302 (e.g., sensor) can measure oxygen or carbon dioxide content in the oral cavity to monitor conditions such as, for example, sleep apnea, where oxygen content will be low.

FIG. 10C is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity (dashed line outlined) disposed at the bottom of positions for alignment adjacent bottoms of top molars, sensors positioned in indentations of the interior surface of the oral appliance for measurements of properties adjacent teeth, and sensors positioned in indentations of the exterior surface of the oral appliance. For example, the data collection device 302 (e.g., sensor) can measure oxygen or carbon dioxide content in the oral cavity to monitor conditions such as, for example, sleep apnea, where oxygen content will be low. Thus, the sensor can be placed in the air flow of the oral cavity and measure the user's respiration rate, especially if the user is breathing very hard through the mouth and if the respiration rate is low an alert will be generated. This is a major advance from a patient wearing a bulky and uncomfortable C-Pap machine or other large intra-oral anti-snoring devices.

Multiplex Sensor

In some embodiments, the oral appliance includes multiplex or a plurality of sensors including temperature sensors, activation sensors, motion sensors, positional sensors, force sensors, radiation sensors, pressure sensors, atmospheric pressure sensors, pulse oximeters capnographs, air-flow sensors, alcohol breathalyzers, and/or saliva sensors. Accordingly, user monitoring system and related biometric data processing methods allows the multiplexing of sensors and data processing.

Pressure sensors can detect if the user is biting down with a sufficient amount of force to ensure proper placement of the oral appliance thereby ensuring optimal protection of the user's jaw and teeth. One or more pressure sensors can be used to determine whether dental appliance is appropriately positioned for taking accurate biometric and/or environmental data.

One or more of these sensors, e.g., pressure sensor(s), and/or motion (force) sensor(s), can also be used to detect usage and non-usage for the purpose of system activation and system power conservation. For example, if the oral appliance has been removed, the inactivity indication can be used to trigger a low-power or sleep-mode, thereby extending the life of the power source.

FIG. 10D is a top plan view of the carrier shell of FIG. 1, which has multiplex sensors, which is shown in a simplified manner lacking intricate detail for simplicity of viewing, indicating one or more components of the oral appliance, such as a data collection device or sensor 302 disposed in the interior of the oral appliance, interface device 304, power supply 306, and processing device 308 (dashed line outlined), disposed at bottom of positions for alignment adjacent bottoms of top molars, positioned in indentations of the interior surface of the oral appliance for measurements of properties adjacent teeth, and positioned in indentations of the exterior surface of the oral appliance for measurements of physical, chemical, biological, and/or environmental information associated with the oral cavity.

Figure 10E:
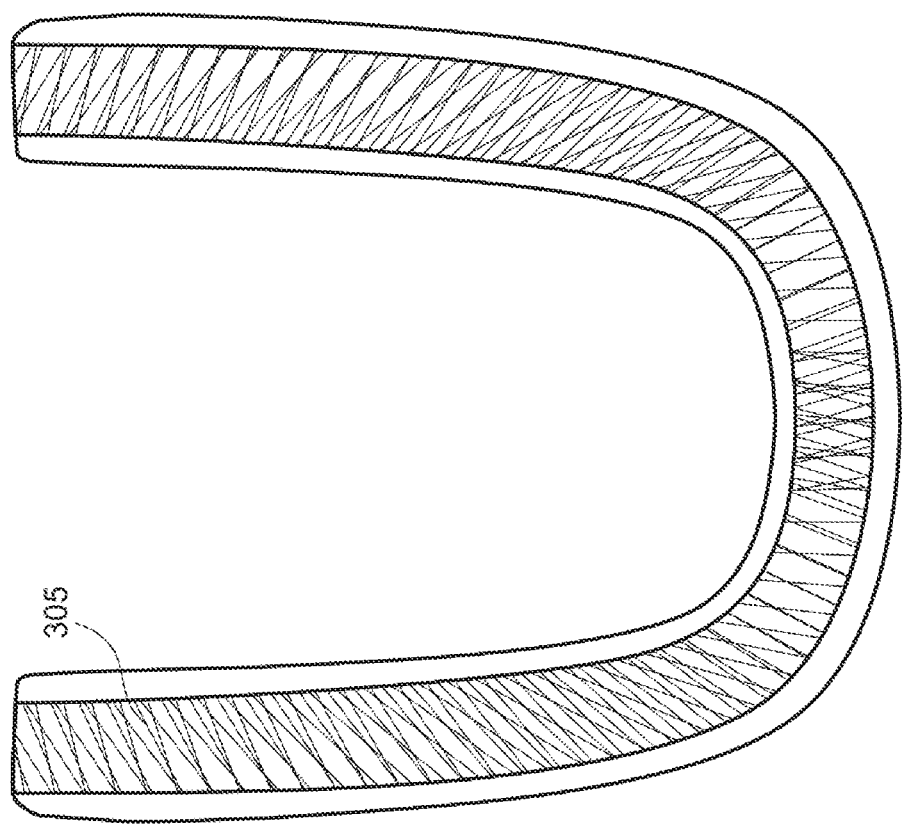
FIG. 10E is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity. In this view, a sensor web is provided in the interior of the device that allows contact with the teeth.

FIG. 10E is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity. In this view, a sensor web 305 is provided in the interior of the device that allows contact with the teeth and can collect data on one or more parameters occurring in the oral cavity. This sensor web can include temperature sensors, activation sensors, motion sensors, positional sensors, force sensors, radiation sensors, pressure sensors, atmospheric pressure sensors, pulse oximeters capnographs, airflow sensors, alcohol breathalyzers, and/or saliva sensors. In some embodiments, the sensor web extends longitudinally in the oral appliance and continuously with the biting surface of the teeth.

Figure 10F:
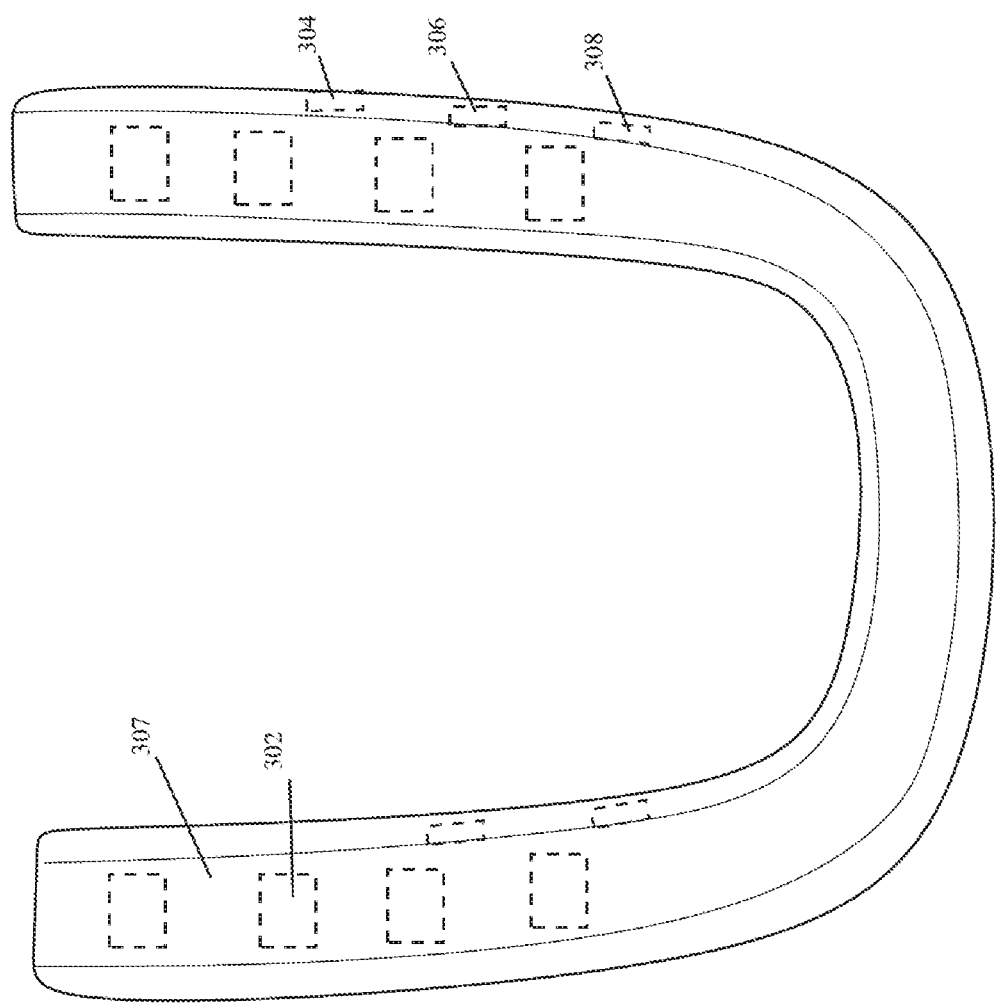
FIG. 10F is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity. In this view, a plurality of data collection devices are disposed in the interior surface and exterior surface of the oral appliance and there is an electroconductive polymer disposed throughout the interior of the oral appliance.

FIG. 10F is a top plan view of the oral appliance of FIG. 1 depicted in a simplified manner lacking intricate detail for simplicity of viewing, indicating various components of the apparatus that monitors physical, chemical, biological, and/or environmental information associated with the oral cavity. In this view, a plurality of data collection devices are disposed in the interior surface and exterior surface of the oral appliance and there is an electroconductive medical polymer 307 disposed throughout the interior of the oral appliance. The data collection device or sensor 302 is disposed in the interior of the oral appliance, interface device 304, power supply 306, and processing device 308 (dashed line outlined) are disposed on the exterior of the oral appliance.

In some embodiments, the electroconductive medical polymer 307 can comprise PermaStat PLUS™ available in acrylic, acrylonitrile butadiene styrene (ABS), polycarbonate/acrylonitrile-butadiene-styrene terpolymer blend (PC/ABS), acetyl, polycarbonate, polyolefins such as polypropylene (PP) and polyethylene (PE) and other resin systems (RTP Company, Winona, Minn.), polymers rendered electrically conductive, such as acetals such as polyoxymethylene (POM), acrylics such as poly(methyl methacrylate) (PMMA), fluoropolymers such as polytetrafluoroethylene (PTFE), polyvinylidene difluoride (PVDF) and perfluoroalkoxy alkanes (PFA), polycarbonate (PC) and PC alloys, polyethereketone (PEEK), polyolefins (PP), (PE), and polymethylpentene (PMP), polysulfone (PSU), polyethersulfone (PES), thermoplastic polyurethane elastomer (TPUR), and styrenics polystyrene (PS) and ABS. In some embodiments, the polymer comprises polypyrrole (PPy), polyaniline (PANI), poly(3,4-ethylenedioxythiophene) (PEDT, PEDOT), polythiophene (PTh), polythiophene-vinylene (PTh-V), poly(2,5-thienylenevinylene) (PTV), poly (3-alkylthiophene) (PAT), poly(p-phenylene) (PPP), poly-p-phenylene-sulphide (PPS), poly(p-phenylenevinylene) (PPV), poly(p-phenylene-terephthalamide) (PPTA), polyacetylene (PAc), poly(isothianaphthene) (PITN), poly(a-naphthylamine) (PNA), polyazulene (PAZ), polyfuran (PFu), polyisoprene (PIP), polybutadiene (PBD), and poly (3-octylthiophnene-3-methylthiophene) (POTMT). Suitable electroconductive polymers that can be used in the device are available from Liquidia Technologies, Inc. and are described in U.S. Pat. No. 8,685,461. This entire disclosure is herein incorporated by reference into the present disclosure. These electroconductive polymers be in microparticle or nanoparticle form and can enhance sensing to and from the data collection device (e.g., sensor, sensor web, sensor array, etc.) by enhancing electrical conduction to and from the data collection device.

Hydrogels

In some embodiments, suitable resins include photocurable hydrogels like poly(ethylene glycols) (PEG) and gelatins. PEG hydrogels have been used to deliver a variety of biological materials, including Growth factors; however, a great challenge facing PEG hydrogels crosslinked by chain growth polymerizations is the potential for irreversible protein damage. Conditions to maximize release of the biologicals from photopolymerized PEG diacrylate hydrogels can be enhanced by inclusion of affinity binding peptide sequences in the monomer resin solutions, prior to photopolymerization allowing sustained delivery. Gelatin is a biopolymer frequently used in food, cosmetic, pharmaceutical and photographic industries. It is obtained by thermal denaturation or chemical and physical degradation of collagen. There are three kinds of gelatin, including those found in animals, fish and humans. Gelatin from the skin of cold water fish is considered safe to use in pharmaceutical applications. UV or visible light can be used to crosslink appropriately modified gelatin.

Three-dimensional oral appliances produced by the methods and processes of the present application may be final, finished or substantially finished products, or may be intermediate products subject to further manufacturing steps such as surface treatment, laser cutting, electric discharge machining, etc. Intermediate products include products for which further additive manufacturing, in the same or a different apparatus, may be carried out. For example, a fault or cleavage line may be introduced deliberately into an ongoing "build" by disrupting, and then reinstating, the gradient of polymerization zone, to terminate one region of the finished product, or simply because a particular region of the finished product or "build" is less fragile than others.

Numerous different oral appliances can be made by the methods and apparatus of the present application, including custom fit oral appliances that correspond to the digital scan taken from the patient's mouth as discussed above.

In some embodiments, the oral appliance has at least one, or a plurality of, pores or channels formed therein. The processes described herein can produce oral appliances with a variety of different properties. Hence in some embodiments the oral appliances are rigid; in other embodiments the products are flexible or resilient. In some embodiments, the oral appliances are a solid; in other embodiments, the oral appliances are a gel such as a hydrogel or have layers of such. In some embodiments, the oral appliances have a shape memory (that is, return substantially to a previous shape after being deformed, so long as they are not deformed to the point of structural failure). In some embodiments, the oral appliances are unitary (that is, formed of a single polymerizable liquid); in some embodiments, the products are composites (that is, formed of two or more different polymerizable liquids). Particular properties will be determined by factors such as the choice of polymerizable liquid(s) employed.

Figure 11:
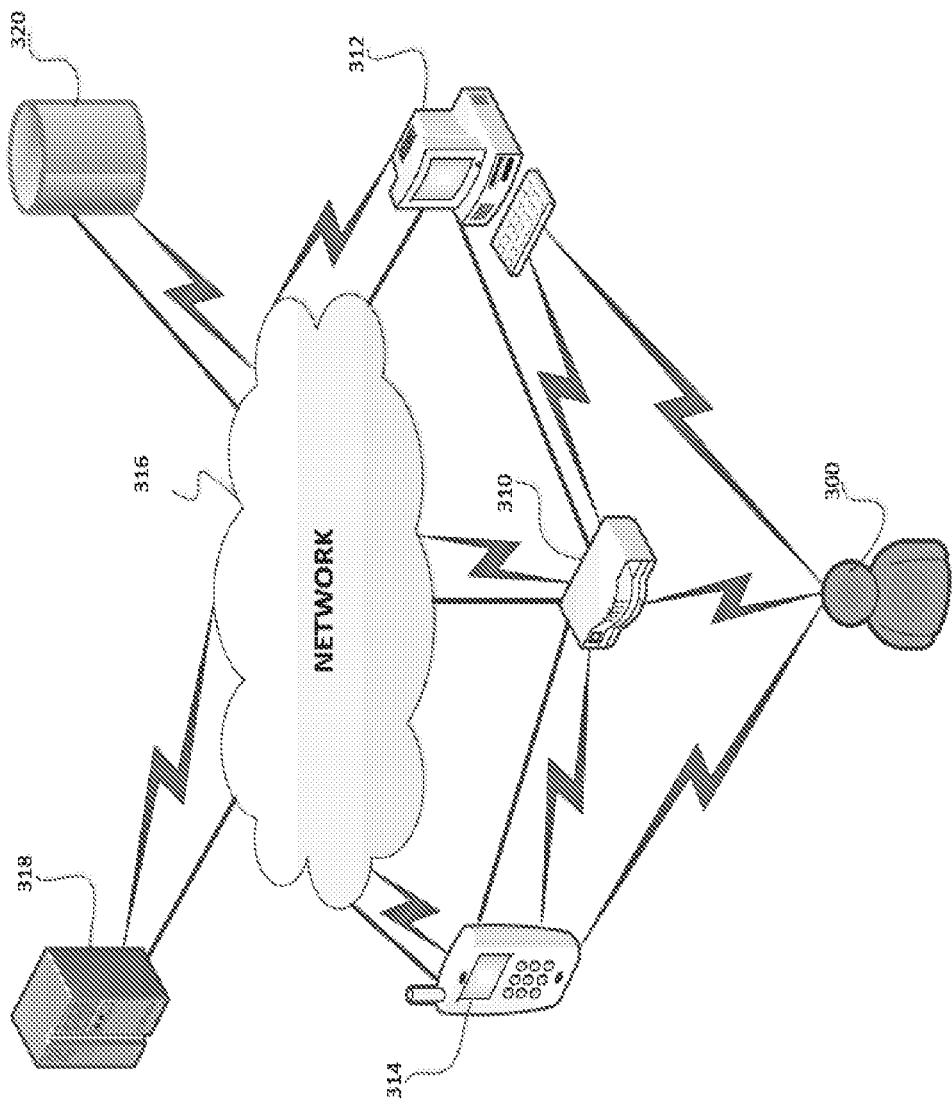
FIG. 11 is a diagram of a system in which the oral appliance is used to monitor, collect, transfer, process, and store physical, chemical, biological, and/or environmental information obtained from the oral cavity.

FIG. 11 is a block diagram of a system in which the oral appliance is used to monitor, collect, transfer, process, and store physical, chemical, biological, and/or environmental information obtained from the oral cavity. The apparatus 300 is applied to a user and wirelessly transfers the information to, for example, a router 310, personal computer 312, phone 314, and/or any other electronic device capable of performing wireless transfers of the information. The router 310, personal computer 312, and/or phone 314 can then further transfer this data to and/or from the router 310, personal computer 312, phone 314, and/or network 316 using wired and/or wireless techniques. This information may be further processed and/or stored via the network 316 by using, for example, the personal computer 312, server 318, and/or database 320. Each of the router 310, phone 314, personal computer 312, network 316 may include capability to receive and/or transmit information from and/or to any other device using wired and/or wireless techniques and/or protocols, such as but not limited to, Bluetooth, Wi-Fi, radio frequency, optical, and/or any other type of wireless communication linkage. The network 312 may be any type of network including, but not limited to, a wide area network, local area network, and/or telephone network.

Figure 12:
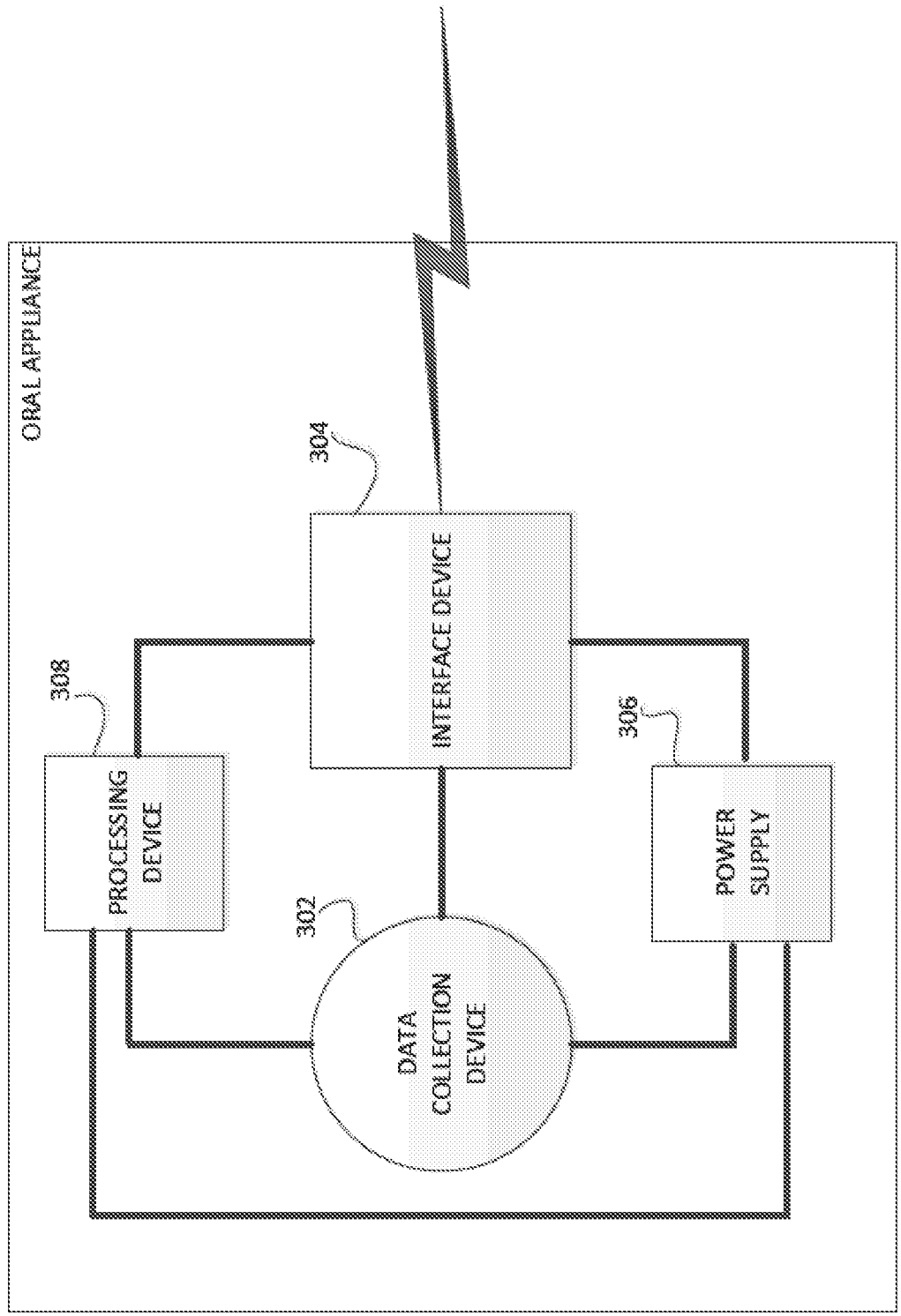
FIG. 12 is a block diagram of an apparatus that monitors information associated with an oral cavity, the apparatus comprising an oral appliance, a data collection device, an interface device coupled to the data collection device, a processing device and a power supply.

FIG. 12 is a block diagram of the oral appliance. The oral appliance includes a data collection device 302, interface device 304, processing device 308, and power supply 306 operatively coupled together using unidirectional and/or bidirectional connections. The data collection device 302 includes one or more sensors designed to monitor physical, chemical, biological, and/or environmental information associated with the oral cavity, and provide this information to the processing device 308 and/or interface device 304. The processing device 308 may perform further processing on the information obtained from the data collection device 302, and provide the processed information to the interface device 304. The interface device 304 is able to wirelessly transfer data between the oral appliance and devices external to the oral appliance, such as the router 310, phone 314, and personal computer 312, and network 316 shown in FIG. 11. The power supply 306 provides power to the data collection device 302, interface device 304, and processing device 308.

The oral appliance may also include a computer-readable storage device (not shown) operatively coupled to at least one of the data collection device, processing device, and/or interface device. The computer-readable storage device is configured to store data provided by the data collection device 302, interface device 304, and/or processing device 308 for subsequent retrieval and/or transmission. The computer-readable storage device may include, for example, Flash memory, RAM, ROM, EEPROM, or any other computer-readable storage medium which can be used to store information.

Figure 13:
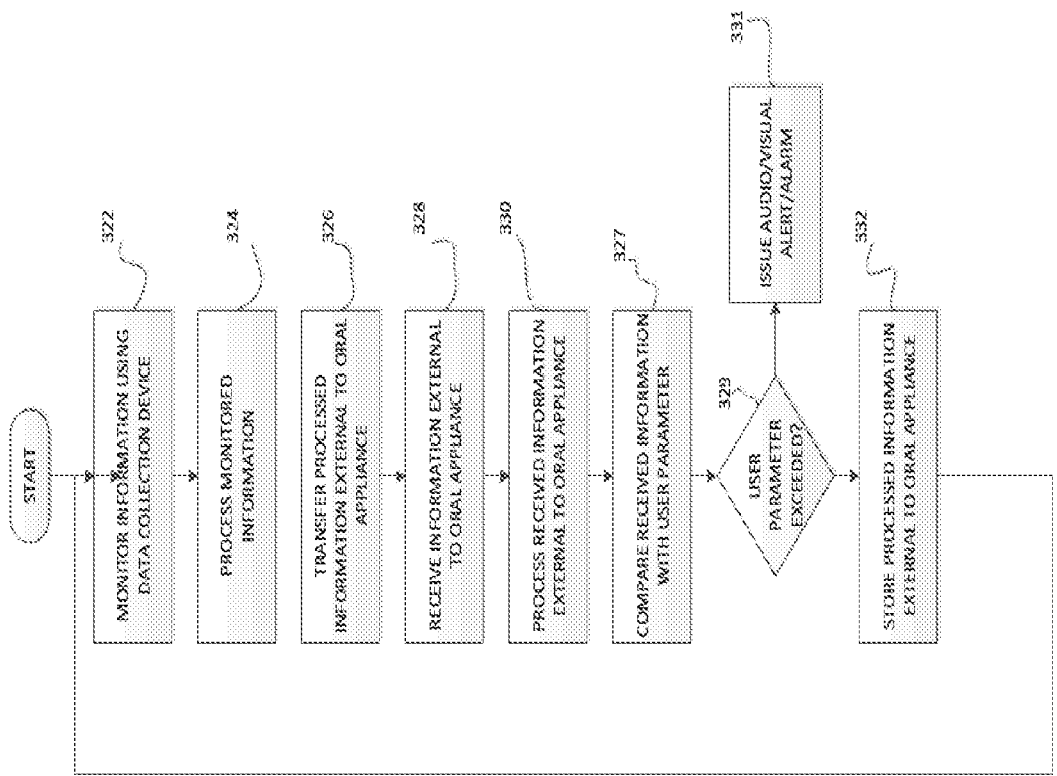
FIG. 13 is a flowchart of one embodiment of instructions for the apparatus that monitors information associated with an oral cavity. First, information is monitored using a data collection device (e.g., sensor). The monitored information is processed and then the processed information is transferred external to the oral appliance. The information is then received external to the oral appliance. The received information is then compared to user parameters. If the user parameters have been exceeded (e.g., increase in pH or carbon dioxide content, decrease in moisture, etc.), then an audio/visual alert or alarm is issued. The processed information is then stored external to the oral appliance.

FIG. 13 is a flowchart illustrating an embodiment of a method in accordance with the disclosure. Information is monitored by the data collection device in the oral cavity in step 322, and the monitored information is optionally processed by the processing device in step 324. The optionally processed information is transferred by the interface device in step 326, and the transferred information is received by one or more devices external to the oral appliance in step 328. The received information is processed by one or more devices external to the oral appliance in step 330, and the processed information is then stored for future access in step 332.

FIG. 14 is a flowchart illustrating another embodiment of a method in accordance with the disclosure. Information is sampled using a sampling medium, such as hydrogel or other absorptive materials, in the oral cavity in step 334, and the sampling medium is removed from the oral appliance in step 336. The sampling medium is processed to obtain information associated with the oral cavity in step 338, and the information is processed by one or more devices external to the oral appliance in step 340. The processed information is then stored for future access in step 342.

Accordingly, the embodiments disclosed herein may take the form of an entirely hardware embodiment, an entirely software embodiment (including firmware, resident software, micro-code, and the like) or an embodiment combining software and hardware aspects that may all generally be referred to herein as a "circuit," "module", or "system." Further, at least a portion of these embodiments may take the form of a computer program product embodied in one or more computer readable medium(s) having computer readable program code embodied thereon.

One or more embodiments, or elements thereof, can be implemented in the form of an apparatus including a storage device or memory and at least one processing device or processor that is coupled to the memory and operative to perform a method according to one or more embodiments.

One or more embodiments disclosed herein, or a portion thereof, make use of software running on a general purpose computer or workstation. By way of example only and without limitation, FIG. 15 is a block diagram of an embodiment of a machine in the form of a computing system 400, within which is a set of instructions 402 that, when executed, cause the machine to perform any one or more of the methodologies according to the disclosed embodiments. In one or more embodiments, the machine operates as a stand-alone device; in one or more other embodiments, the machine is connected (e.g., via a network 422) to other machines. In a networked implementation, the machine operates in the capacity of a server or a client user machine in a server-client user network environment. Exemplary implementations of the machine, as contemplated by embodiments disclosed herein, include but are not limited to, a server computer, client user computer, personal computer (PC), tablet PC, personal digital assistant (PDA), cellular telephone, mobile device, palmtop computer, laptop computer, desktop computer, communication device, personal trusted device, web appliance, network router, switch or bridge, or any machine capable of executing a set of instructions (sequential or otherwise) that specify actions to be taken by that machine.

The computing system 400 includes a processing device(s) 404 (e.g., a central processing unit (CPU), a graphics processing unit (GPU), or both), program memory device(s) 406, and data memory device(s) 408, which communicate with each other via a bus 410. The computing system 400 further includes display device(s) 412 (e.g., liquid crystals display (LCD), flat panel, solid state display, or cathode ray tube (CRT)). The computing system 400 includes input device(s) 414 (e.g., a keyboard), cursor control device(s) 416 (e.g., a mouse), disk drive unit(s) 418, signal generation device(s) 420 (e.g., a speaker or remote control), and network interface device(s) 424, operatively coupled together, and/or with other functional blocks, via bus 410.

The disk drive unit(s) 418 includes machine-readable medium(s) 426, on which is stored one or more sets of instructions 402 (e.g., software) embodying any one or more of the methodologies or functions herein, including those methods illustrated herein. The instructions 402 may also reside, completely or at least partially, within the program memory device(s) 406, the data memory device(s) 408, and/or the processing device(s) 404 during execution thereof by the computing system 400. The program memory device(s) 406 and the processing device(s) 404 also constitute machine-readable media. Dedicated hardware implementations, such as but not limited to ASICs (Application Specific Integrated Circuits), programmable logic arrays, and other hardware devices can likewise be constructed to implement methods described herein. Applications that include the apparatus and systems of various embodiments broadly comprise a variety of electronic and computer systems. Some embodiments implement functions in two or more specific interconnected hardware modules or devices with related control and data signals communicated between and through the modules, or as portions of an ASIC. Thus, the example system is applicable to software, firmware, and/or hardware implementations.

The term "processing device" as used herein is intended to include any processor, such as, for example, one that includes a CPU (central processing unit) and/or other forms of processing circuitry. Further, the term "processing device" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s) 412, input device(s) 414, cursor control device(s) 416, signal generation device(s) 420, etc., can be collectively referred to as an "input/output interface," and is intended to include one or more mechanisms for inputting data to the processing device(s) 404, and one or more mechanisms for providing results associated with the processing device(s). Input/output or I/O devices including but not limited to keyboards (e.g., alpha-numeric input device(s) 414, display device(s) 412, and the like) can be coupled to the system either directly (such as via bus 410) or through intervening input/output controllers (omitted for clarity).

In an integrated circuit implementation of one or more embodiments of the disclosure, multiple identical die are typically fabricated in a repeated pattern on a surface of a semiconductor wafer. Each such die may include a device described herein, and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this specification.

An integrated circuit in accordance with the embodiments of the disclosed embodiments can be employed in essentially any application and/or electronic system in which buffers are utilized. Suitable systems for implementing one or more embodiments of the disclosed embodiments include, but are not limited, to personal computers, interface devices (e.g., interface networks, high-speed memory interfaces (e.g., DDR3, DDR4), etc.), data storage systems (e.g., RAID system), data servers, etc. Systems incorporating such integrated circuits are considered part of the disclosed embodiments. Given the teachings provided herein, one of ordinary skill in the art will be able to contemplate other implementations and applications.

In accordance with various embodiments, the methods, functions or logic described herein are implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

The embodiment contemplates a machine-readable medium or computer-readable medium containing instructions 302, or that which receives and executes instructions 302 from a propagated signal so that a device connected to a network environment 322 can send or receive voice, video or data, and to communicate over the network 322 using the instructions 302. The instructions 302 are further transmitted or received over the network 322 via the network interface device(s) 324. The machine-readable medium also contains a data structure for storing data useful in providing a functional relationship between the data and a machine or computer in an illustrative embodiment of the systems and methods herein.

While the machine-readable medium 302 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform anyone or more of the methodologies of the embodiment. The term "machine-readable medium" shall accordingly be taken to include, but not be limited to: solid-state memory (e.g., solid-state drive (SSD), flash memory, etc.); read-only memory (ROM), or other non-volatile memory; random access memory (RAM), or other re-writable (volatile) memory; magneto-optical or optical medium, such as a disk or tape; and/or a digital file attachment to e-mail or other self-contained information archive or set of archives is considered a distribution medium equivalent to a tangible storage medium. Accordingly, the embodiment is considered to include anyone or more of a tangible machine-readable medium or a tangible distribution medium, as listed herein and including art-recognized equivalents and successor media, in which the software implementations herein are stored.

It should also be noted that software, which implements the methods, functions and/or logic herein, are optionally stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

As previously stated, although the specification describes components and functions implemented in accordance with embodiments of the disclosure with reference to particular standards and protocols, the embodiments are not limited to such standards and protocols.

The illustrations of embodiments of the disclosure described herein are intended to provide a general understanding of the structure of various embodiments, and they are not intended to serve as a complete description of all the elements and features of apparatus and systems that might make use of the structures described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments are referred to herein, individually and/or collectively, by the term "embodiment" merely for convenience and without intending to limit the scope of this application to any single embodiment or concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, disclosed subject matter lies in less than all features of a single embodiment. Thus the following claims are hereby incorporated into the Detailed Description, with each claim standing on its own as a separate example embodiment.

Given the teachings of the disclosure provided herein, one of ordinary skill in the art will be able to contemplate other implementations and applications of the techniques of the disclosure. Although illustrative embodiments of the disclosure have been described herein with reference to the accompanying drawings, it is to be understood that the disclosure is not limited to those precise embodiments, and that various other changes and modifications are made therein by one skilled in the art without departing from the scope of the appended claims.

While particular embodiments of the present disclosure have been shown and described, it will be appreciated by those skilled in the art that, based upon the teachings herein, changes and modifications may be made without departing from this disclosure and its broader aspects and, therefore, the appended claims are to encompass within their scope all such changes and modifications as are within the true spirit and scope of this disclosure. The true spirit and scope is considered to encompass devices and processes, unless specifically limited to distinguish from known subject matter, which provide equivalent functions as required for interaction with other elements of the claims and the scope is not considered limited to devices and functions currently in existence where future developments may supplant usage of currently available devices and processes yet provide the functioning required for interaction with other claim elements. Furthermore, it is to be understood that the disclosure is solely defined by the appended claims.

What is claimed is:

1. A computer implemented method of producing an oral appliance containing a discrete region for placing a sensor to collect biological information about a patient's oral cavity, the computer implemented method comprising: generating first digital data representing at least a portion of teeth and/or soft tissue areas of the oral cavity of the patient, the first digital data generated from an imaging device having a base image of the oral cavity; and generating second digital data from the base image by performing an additive layer of at least a portion of the teeth and/or soft tissues areas of the oral cavity to determine the discrete region of the oral cavity to place the sensor, combining the first digital data (Dig1) and the second digital data (Dig2) to form a third digital data (Dig3) from which the oral appliance can be produced into 3D printing data, wherein the discrete region to place the sensor corresponds to the second digital data (Dig2) and the second digital data (Dig2) is added onto or subtracted from the first digital data (Dig1) to form the third digital data (Dig3) such that the Dig3 includes the discrete region, which extends longitudinally and continuously for the placement of the sensor such that the sensor extends along the discrete region as a sensor web to contact the soft tissue areas of the oral cavity.

2. A computer implemented method of claim 1, wherein the method further comprises operating a manufacturing system to produce the oral appliance including the discrete region for placing the sensor.

3. A computer implemented method of claim 1, wherein the discrete region for placing the sensor comprises a cargo area configured to house the sensor.

4. A computer implemented method of claim 1, wherein the sensor is positioned to detect biological characteristics including temperature, pH, $O_2$, and $CO_2$.

5. A computer system for making an oral appliance containing a discrete region for placing a sensor to collect biological information about a patient's oral cavity, the computer system comprising logic encoded in the computer for generating a first digital data (Dig1) representing at least a portion of teeth and/or soft tissue areas of the oral cavity of the patient, the first digital data is layered onto a Base Image recorded by an imaging device; logic encoded in the computer for generating a second digital data (Dig2) by performing an additive layer of at least a portion of the teeth and/or soft tissue areas of the oral cavity to determine the discrete region of the oral cavity to place the sensor; logic encoded in the computer for combining the first digital data and the second digital data to form a third digital data (Dig3) from which the oral appliance can be produced, wherein the discrete region to place the sensor corresponds to the second digital data (Dig2) and the second digital data (Dig2) is added onto or subtracted from the first digital data (Dig1) to form the third digital data (Dig3) such that the Dig3 includes the discrete region extending longitudinally and continuously for the placement of the sensor such that the sensor extends along the discrete region as a sensor web to contact the soft tissue areas of the oral cavity.

6. A computer system for making an oral appliance according to claim 5, further comprising logic encoded in the computer to initiate a manufacturing sequence to manufacture the oral appliance from the third digital data.

\* \* \* \* \*